United States Patent
Majcher

(10) Patent No.: US 12,195,338 B2
(45) Date of Patent: Jan. 14, 2025

(54) SYSTEMS, METHODS, AND DEVICE FOR PYROLYSIS OF METHANE IN A MICROWAVE PLASMA FOR HYDROGEN AND STRUCTURED CARBON POWDER PRODUCTION

(71) Applicant: 6K Inc., North Andover, MA (US)

(72) Inventor: Jared Majcher, Portsmouth, NH (US)

(73) Assignee: 6K Inc., North Andover, MA (US)

( * ) Notice: Subject to any disclaimer, the term of this patent is extended or adjusted under 35 U.S.C. 154(b) by 0 days.

(21) Appl. No.: 18/494,522

(22) Filed: Oct. 25, 2023

(65) Prior Publication Data
US 2024/0199427 A1    Jun. 20, 2024

Related U.S. Application Data

(60) Provisional application No. 63/387,669, filed on Dec. 15, 2022.

(51) Int. Cl.
*C01B 32/184* (2017.01)
*C01B 3/24* (2006.01)
(Continued)

(52) U.S. Cl.
CPC .............. *C01B 32/184* (2017.08); *C01B 3/24* (2013.01); *C07C 2/78* (2013.01); *H05H 1/30* (2013.01);
(Continued)

(58) Field of Classification Search
CPC ........... C01B 32/184; C01B 3/24; C07C 2/78; H05H 1/30; H05H 2245/10; C01C 2203/0855
(Continued)

(56) References Cited

U.S. PATENT DOCUMENTS

| 1,699,205 A | 1/1929 | Emil et al. |
| 2,892,215 A | 6/1959 | Gerhard et al. |

(Continued)

FOREIGN PATENT DOCUMENTS

| AU | 2003211869 A1 | 9/2003 |
| AU | 2014394102 B2 | 6/2020 |

(Continued)

OTHER PUBLICATIONS

Ghosh, A., et al., "Carbon nanotube-glass composite with high dielectric constant and low dielectric loss for energy storage device applications", Physics and Chemistry of Glasses—European Journal of Glass Science and Technology Part B, vol. 64, No. 1, Feb. 1, 2023, 1 page.

(Continued)

*Primary Examiner* — Colin W. Slifka
(74) *Attorney, Agent, or Firm* — Knobbe, Martens, Olson & Bear, LLP

(57) ABSTRACT

The embodiments disclosed herein are directed to systems, methods, and devices for pyrolysis of methane in a microwave plasma for hydrogen production and structured carbon powder. Some methods are directed to producing a structured carbon powder using a microwave generated plasma comprising injecting a plasma gas comprising methane ($CH_4$) into a liner, the liner in communication with a microwave waveguide; propagating microwaves through the microwave waveguide, the microwaves generated using a microwave generator; and generating a microwave plasma by contacting the plasma gas with the microwaves.

18 Claims, 12 Drawing Sheets

(51) Int. Cl.
*C07C 2/78* (2006.01)
*H05H 1/30* (2006.01)

(52) U.S. Cl.
CPC .......... C01B 2203/0272 (2013.01); C01B 2203/0855 (2013.01); C01B 2203/0861 (2013.01); C01B 2203/1241 (2013.01); C01P 2002/72 (2013.01); C01P 2004/03 (2013.01); H05H 2245/10 (2021.05)

(58) Field of Classification Search
USPC .................................................. 423/461
See application file for complete search history.

(56) References Cited

U.S. PATENT DOCUMENTS

| | | |
|---|---|---|
| 3,290,723 A | 12/1966 | John et al. |
| 3,293,334 A | 12/1966 | Bylund et al. |
| 3,434,831 A | 3/1969 | Knopp |
| 3,466,165 A | 9/1969 | Rhys et al. |
| RE26,879 E | 5/1970 | Kelso |
| 3,652,259 A | 3/1972 | Knopp |
| 3,802,816 A | 4/1974 | Kaufmann |
| 3,845,344 A | 10/1974 | Rainer |
| 3,909,241 A | 9/1975 | Cheney et al. |
| 3,966,374 A | 6/1976 | Honnorat et al. |
| 3,974,245 A | 8/1976 | Cheney et al. |
| 4,076,640 A | 2/1978 | Forgensi et al. |
| 4,177,026 A | 12/1979 | Honnorat et al. |
| 4,212,837 A | 7/1980 | Kubo et al. |
| 4,221,554 A | 9/1980 | Oguchi et al. |
| 4,221,775 A | 9/1980 | Anno |
| 4,265,730 A | 5/1981 | Hirose et al. |
| 4,423,303 A | 12/1983 | Hirose et al. |
| 4,431,449 A | 2/1984 | Dillon et al. |
| 4,439,410 A | 3/1984 | Santen et al. |
| 4,544,404 A | 10/1985 | Yolton et al. |
| 4,569,823 A | 2/1986 | Westin |
| 4,599,880 A | 7/1986 | Stepanenko et al. |
| 4,611,108 A | 9/1986 | Leprince et al. |
| 4,670,047 A | 6/1987 | Kopatz et al. |
| 4,692,584 A | 9/1987 | Caneer, Jr. |
| 4,705,560 A | 11/1987 | Kemp et al. |
| 4,711,660 A | 12/1987 | Kemp et al. |
| 4,711,661 A | 12/1987 | Kemp et al. |
| 4,714,587 A | 12/1987 | Eylon et al. |
| 4,731,110 A | 3/1988 | Kopatz et al. |
| 4,731,111 A | 3/1988 | Kopatz et al. |
| 4,772,315 A | 9/1988 | Johnson et al. |
| 4,778,515 A | 10/1988 | Kemp et al. |
| 4,780,131 A | 10/1988 | Kemp et al. |
| 4,780,881 A | 10/1988 | Zhang et al. |
| 4,783,216 A | 11/1988 | Kemp et al. |
| 4,783,218 A | 11/1988 | Kemp et al. |
| 4,787,934 A | 11/1988 | Johnson et al. |
| 4,802,915 A | 2/1989 | Kopatz et al. |
| 4,836,850 A | 6/1989 | Kemp et al. |
| 4,859,237 A | 8/1989 | Johnson et al. |
| 4,923,509 A | 5/1990 | Kemp et al. |
| 4,923,531 A | 5/1990 | Fisher |
| 4,943,322 A | 7/1990 | Kemp et al. |
| 4,944,797 A | 7/1990 | Kemp et al. |
| 4,952,389 A | 8/1990 | Szymanski et al. |
| 5,022,935 A | 6/1991 | Fisher |
| 5,032,202 A | 7/1991 | Tsai et al. |
| 5,041,713 A | 8/1991 | Weidman |
| 5,095,048 A | 3/1992 | Takahashi et al. |
| 5,114,471 A | 5/1992 | Johnson et al. |
| 5,131,992 A | 7/1992 | Church et al. |
| 5,200,595 A | 4/1993 | Boulos et al. |
| 5,234,526 A | 8/1993 | Chen et al. |
| 5,290,507 A | 3/1994 | Runkle |
| 5,292,370 A | 3/1994 | Tsai et al. |
| 5,370,765 A | 12/1994 | Dandl |
| 5,376,475 A | 12/1994 | Ovshinsky et al. |
| 5,395,453 A | 3/1995 | Noda |
| 5,411,592 A | 5/1995 | Ovshinsky et al. |
| 5,431,967 A | 7/1995 | Manthiram et al. |
| 5,518,831 A | 5/1996 | Tou et al. |
| 5,567,243 A | 10/1996 | Foster et al. |
| 5,665,640 A | 9/1997 | Foster et al. |
| 5,671,045 A | 9/1997 | Woskov et al. |
| 5,676,919 A | 10/1997 | Kawamura et al. |
| 5,750,013 A | 5/1998 | Lin |
| 5,776,323 A | 7/1998 | Kobashi |
| 5,866,213 A | 2/1999 | Foster et al. |
| 5,876,684 A | 3/1999 | Withers et al. |
| 5,909,277 A | 6/1999 | Woskov et al. |
| 5,958,361 A | 9/1999 | Laine et al. |
| 5,969,352 A | 10/1999 | French et al. |
| 5,980,977 A | 11/1999 | Deng et al. |
| 5,989,648 A | 11/1999 | Phillips |
| 6,027,585 A | 2/2000 | Patterson et al. |
| 6,200,651 B1 | 3/2001 | Roche et al. |
| 6,221,125 B1 | 4/2001 | Soda et al. |
| 6,261,484 B1 | 7/2001 | Phillips et al. |
| 6,274,110 B1 | 8/2001 | Kim et al. |
| 6,329,628 B1 | 12/2001 | Kuo et al. |
| 6,334,882 B1 | 1/2002 | Christer |
| 6,362,449 B1 | 3/2002 | Hadidi et al. |
| 6,376,027 B1 | 4/2002 | Lee et al. |
| 6,409,851 B1 | 6/2002 | Sethuram et al. |
| 6,428,600 B1 | 8/2002 | Flurschuetz et al. |
| 6,543,380 B1 | 4/2003 | Sung-Spitzl |
| 6,551,377 B1 | 4/2003 | Leonhardt |
| 6,569,397 B1 | 5/2003 | Yadav et al. |
| 6,579,573 B2 | 6/2003 | Strutt et al. |
| 6,589,311 B1 | 7/2003 | Han et al. |
| 6,607,693 B1 | 8/2003 | Saito et al. |
| 6,652,822 B2 | 11/2003 | Phillips et al. |
| 6,652,923 B2 | 11/2003 | Uemura et al. |
| 6,676,728 B2 | 1/2004 | Han et al. |
| 6,689,192 B1 | 2/2004 | Phillips et al. |
| 6,752,979 B1 | 6/2004 | Talbot et al. |
| 6,755,886 B2 | 6/2004 | Phillips et al. |
| 6,780,219 B2 | 8/2004 | Singh et al. |
| 6,793,849 B1 | 9/2004 | Gruen et al. |
| 6,805,822 B2 | 10/2004 | Takei et al. |
| 6,838,072 B1 | 1/2005 | Kong et al. |
| 6,869,550 B2 | 3/2005 | Dorfman et al. |
| 6,902,745 B2 | 6/2005 | Lee et al. |
| 6,919,257 B2 | 7/2005 | Gealy et al. |
| 6,919,527 B2 | 7/2005 | Boulos et al. |
| 6,989,529 B2 | 1/2006 | Wiseman |
| 7,066,980 B2 | 6/2006 | Akimoto et al. |
| 7,091,441 B1 | 8/2006 | Kuo |
| 7,108,733 B2 | 9/2006 | Enokido |
| 7,125,537 B2 | 10/2006 | Liao et al. |
| 7,125,822 B2 | 10/2006 | Nakano et al. |
| 7,175,786 B2 | 2/2007 | Celikkaya et al. |
| 7,182,929 B1 | 2/2007 | Singhal et al. |
| 7,220,398 B2 | 5/2007 | Sutorik et al. |
| 7,235,118 B2 | 6/2007 | Bouaricha et al. |
| 7,285,194 B2 | 10/2007 | Uno et al. |
| 7,285,307 B2 | 10/2007 | Hohenthanner et al. |
| 7,297,310 B1 | 11/2007 | Peng et al. |
| 7,297,892 B2 | 11/2007 | Kelley et al. |
| 7,344,776 B2 | 3/2008 | Kollmann et al. |
| 7,357,910 B2 | 4/2008 | Phillips et al. |
| 7,368,130 B2 | 5/2008 | Kim et al. |
| 7,374,704 B2 | 5/2008 | Che et al. |
| 7,375,303 B2 | 5/2008 | Twarog |
| 7,381,496 B2 | 6/2008 | Onnerud et al. |
| 7,431,750 B2 | 10/2008 | Liao et al. |
| 7,442,271 B2 | 10/2008 | Asmussen et al. |
| 7,491,468 B2 | 2/2009 | Okada et al. |
| 7,517,513 B2 | 4/2009 | Sarkas et al. |
| 7,524,353 B2 | 4/2009 | Johnson et al. |
| 7,534,296 B2 | 5/2009 | Swain et al. |
| 7,572,315 B2 | 8/2009 | Boulos et al. |
| 7,622,211 B2 | 11/2009 | Vyas et al. |
| 7,629,553 B2 | 12/2009 | Fanson et al. |
| 7,670,203 B2 | 3/2010 | Gammel et al. |
| 7,700,152 B2 | 4/2010 | Laine et al. |

(56) References Cited

U.S. PATENT DOCUMENTS

| | | |
|---|---|---|
| 7,776,303 B2 | 8/2010 | Hung et al. |
| 7,806,077 B2 | 10/2010 | Lee et al. |
| 7,828,999 B2 | 11/2010 | Yubuta et al. |
| 7,901,658 B2 | 3/2011 | Weppner et al. |
| 7,931,836 B2 | 4/2011 | Xie et al. |
| 7,939,141 B2 | 5/2011 | Matthews et al. |
| 8,007,691 B2 | 8/2011 | Sawaki et al. |
| 8,043,405 B2 | 10/2011 | Johnson et al. |
| 8,092,941 B2 | 1/2012 | Weppner et al. |
| 8,101,061 B2 | 1/2012 | Suh et al. |
| 8,168,128 B2 | 5/2012 | Seeley et al. |
| 8,178,240 B2 | 5/2012 | Wang et al. |
| 8,192,865 B2 | 6/2012 | Buiel et al. |
| 8,193,291 B2 | 6/2012 | Zhang |
| 8,211,388 B2 | 7/2012 | Woodfield et al. |
| 8,221,853 B2 | 7/2012 | Marcinek et al. |
| 8,268,230 B2 | 9/2012 | Cherepy et al. |
| 8,283,275 B2 | 10/2012 | Heo et al. |
| 8,303,926 B1 | 11/2012 | Luhrs et al. |
| 8,329,090 B2 | 12/2012 | Hollingsworth et al. |
| 8,329,257 B2 | 12/2012 | Larouche et al. |
| 8,338,323 B2 | 12/2012 | Takasu et al. |
| 8,372,369 B2 | 2/2013 | Yang et al. |
| 8,389,160 B2 | 3/2013 | Venkatachalam et al. |
| 8,420,043 B2 | 4/2013 | Gamo et al. |
| 8,439,998 B2 | 5/2013 | Ito et al. |
| 8,449,950 B2 | 5/2013 | Shang et al. |
| 8,478,785 B2 | 7/2013 | Jamjoom et al. |
| 8,492,303 B2 | 7/2013 | Bulan et al. |
| 8,529,996 B2 | 9/2013 | Bocian et al. |
| 8,592,767 B2 | 11/2013 | Rappe et al. |
| 8,597,722 B2 | 12/2013 | Albano et al. |
| 8,623,555 B2 | 1/2014 | Kang et al. |
| 8,658,317 B2 | 2/2014 | Weppner et al. |
| 8,685,593 B2 | 4/2014 | Dadheech et al. |
| 8,728,680 B2 | 5/2014 | Mikhail et al. |
| 8,735,022 B2 | 5/2014 | Schlag et al. |
| 8,748,785 B2 | 6/2014 | Jordan et al. |
| 8,758,957 B2 | 6/2014 | Dadheech et al. |
| 8,784,706 B2 | 7/2014 | Shevchenko et al. |
| 8,822,000 B2 | 9/2014 | Kumagai et al. |
| 8,840,701 B2 | 9/2014 | Borland et al. |
| 8,853,932 B2 | 10/2014 | Kar et al. |
| 8,877,119 B2 | 11/2014 | Jordan et al. |
| 8,911,529 B2 | 12/2014 | Withers et al. |
| 8,919,428 B2 | 12/2014 | Cola et al. |
| 8,945,431 B2 | 2/2015 | Schulz et al. |
| 8,951,496 B2 | 2/2015 | Hadidi et al. |
| 8,956,785 B2 | 2/2015 | Dadheech et al. |
| 8,968,587 B2 | 3/2015 | Shin et al. |
| 8,968,669 B2 | 3/2015 | Chen |
| 8,980,485 B2 | 3/2015 | Lanning et al. |
| 8,999,440 B2 | 4/2015 | Zenasni et al. |
| 9,023,259 B2 | 5/2015 | Hadidi et al. |
| 9,051,647 B2 | 6/2015 | Cooperberg et al. |
| 9,065,141 B2 | 6/2015 | Merzougui et al. |
| 9,067,264 B2 | 6/2015 | Moxson et al. |
| 9,079,778 B2 | 7/2015 | Kelley et al. |
| 9,085,490 B2 | 7/2015 | Taylor et al. |
| 9,101,982 B2 | 8/2015 | Christer |
| 9,136,569 B2 | 9/2015 | Song et al. |
| 9,150,422 B2 | 10/2015 | Nakayama et al. |
| 9,193,133 B2 | 11/2015 | Shin et al. |
| 9,196,901 B2 | 11/2015 | Se-Hee et al. |
| 9,196,905 B2 | 11/2015 | Tzeng et al. |
| 9,206,085 B2 | 12/2015 | Hadidi et al. |
| 9,242,224 B2 | 1/2016 | Redjdal et al. |
| 9,259,785 B2 | 2/2016 | Hadidi et al. |
| 9,293,302 B2 | 3/2016 | Risby et al. |
| 9,321,071 B2 | 4/2016 | Jordan et al. |
| 9,322,081 B2 | 4/2016 | McHugh et al. |
| 9,352,278 B2 | 5/2016 | Spatz et al. |
| 9,356,281 B2 | 5/2016 | Verbrugge et al. |
| 9,368,772 B1 | 6/2016 | Chen et al. |
| 9,378,928 B2 | 6/2016 | Zeng et al. |
| 9,412,998 B2 | 8/2016 | Rojeski et al. |
| 9,421,612 B2 | 8/2016 | Fang et al. |
| 9,425,463 B2 | 8/2016 | Hsu et al. |
| 9,463,435 B2 | 10/2016 | Schulz et al. |
| 9,463,984 B2 | 10/2016 | Sun et al. |
| 9,520,593 B2 | 12/2016 | Sun et al. |
| 9,520,600 B2 | 12/2016 | Dadheech et al. |
| 9,624,565 B2 | 4/2017 | Lee et al. |
| 9,630,162 B1 | 4/2017 | Sunkara et al. |
| 9,643,891 B2 | 5/2017 | Hadidi et al. |
| 9,700,877 B2 | 7/2017 | Kim et al. |
| 9,705,136 B2 | 7/2017 | Rojeski |
| 9,718,131 B2 | 8/2017 | Boulos et al. |
| 9,735,427 B2 | 8/2017 | Zhang |
| 9,738,788 B1 | 8/2017 | Gross et al. |
| 9,751,129 B2 | 9/2017 | Boulos et al. |
| 9,767,990 B2 | 9/2017 | Zeng et al. |
| 9,768,033 B2 | 9/2017 | Ranjan et al. |
| 9,776,378 B2 | 10/2017 | Choi |
| 9,782,791 B2 | 10/2017 | Redjdal et al. |
| 9,782,828 B2 | 10/2017 | Wilkinson |
| 9,796,019 B2 | 10/2017 | She et al. |
| 9,796,020 B2 | 10/2017 | Aslund |
| 9,831,503 B2 | 11/2017 | Sopchak |
| 9,871,248 B2 | 1/2018 | Rayner et al. |
| 9,879,344 B2 | 1/2018 | Lee et al. |
| 9,899,674 B2 | 2/2018 | Hirai et al. |
| 9,917,299 B2 | 3/2018 | Behan et al. |
| 9,932,673 B2 | 4/2018 | Jordan et al. |
| 9,945,034 B2 | 4/2018 | Yao et al. |
| 9,945,564 B2 | 4/2018 | Gao et al. |
| 9,947,926 B2 | 4/2018 | Kim et al. |
| 9,981,284 B2 | 5/2018 | Guo et al. |
| 9,991,458 B2 | 6/2018 | Rosenman et al. |
| 9,999,922 B1 | 6/2018 | Struve |
| 10,011,491 B2 | 7/2018 | Lee et al. |
| 10,050,303 B2 | 8/2018 | Anandan et al. |
| 10,057,986 B2 | 8/2018 | Prud'Homme et al. |
| 10,065,240 B2 | 9/2018 | Chen |
| 10,079,392 B2 | 9/2018 | Huang et al. |
| 10,116,000 B1 | 10/2018 | Federici et al. |
| 10,130,994 B2 | 11/2018 | Fang et al. |
| 10,167,556 B2 | 1/2019 | Ruzic et al. |
| 10,170,753 B2 | 1/2019 | Ren et al. |
| 10,193,142 B2 | 1/2019 | Rojeski |
| 10,244,614 B2 | 3/2019 | Foret |
| 10,279,531 B2 | 5/2019 | Pagliarini |
| 10,283,757 B2 | 5/2019 | Noh et al. |
| 10,319,537 B2 | 6/2019 | Claussen et al. |
| 10,333,183 B2 | 6/2019 | Sloop |
| 10,350,680 B2 | 7/2019 | Yamamoto et al. |
| 10,403,475 B2 | 9/2019 | Cooperberg et al. |
| 10,411,253 B2 | 9/2019 | Tzeng et al. |
| 10,439,206 B2 | 10/2019 | Behan et al. |
| 10,442,000 B2 | 10/2019 | Fukada et al. |
| 10,461,298 B2 | 10/2019 | Herle |
| 10,472,497 B2 | 11/2019 | Stowell et al. |
| 10,477,665 B2 | 11/2019 | Hadidi et al. |
| 10,493,524 B2 | 12/2019 | She et al. |
| 10,502,705 B2 | 12/2019 | Stowell et al. |
| 10,522,300 B2 | 12/2019 | Yang |
| 10,526,684 B2 | 1/2020 | Ekman et al. |
| 10,529,486 B2 | 1/2020 | Nishisaka |
| 10,543,534 B2 | 1/2020 | Hadidi et al. |
| 10,584,923 B2 | 3/2020 | De et al. |
| 10,593,985 B2 | 3/2020 | Sastry et al. |
| 10,610,929 B2 | 4/2020 | Fang et al. |
| 10,637,029 B2 | 4/2020 | Gotlib Vainshtein et al. |
| 10,638,592 B2 | 4/2020 | Foret |
| 10,639,712 B2 | 5/2020 | Barnes et al. |
| 10,647,824 B2 | 5/2020 | Hwang et al. |
| 10,655,206 B2 | 5/2020 | Moon et al. |
| 10,665,890 B2 | 5/2020 | Kang et al. |
| 10,668,566 B2 | 6/2020 | Smathers et al. |
| 10,669,437 B2 | 6/2020 | Cox et al. |
| 10,688,564 B2 | 6/2020 | Boulos et al. |
| 10,707,477 B2 | 7/2020 | Sastry et al. |
| 10,717,150 B2 | 7/2020 | Aleksandrov et al. |
| 10,727,477 B2 | 7/2020 | Kim et al. |

(56) References Cited

U.S. PATENT DOCUMENTS

| | | |
|---|---|---|
| 10,741,845 B2 | 8/2020 | Yushin et al. |
| 10,744,590 B2 | 8/2020 | Maier et al. |
| 10,756,334 B2 | 8/2020 | Stowell et al. |
| 10,766,787 B1 | 9/2020 | Sunkara et al. |
| 10,777,804 B2 | 9/2020 | Sastry et al. |
| 10,781,103 B2 | 9/2020 | Tanner et al. |
| 10,837,102 B2 | 11/2020 | Boyd et al. |
| 10,858,255 B2 | 12/2020 | Koziol et al. |
| 10,858,500 B2 | 12/2020 | Chen et al. |
| 10,892,477 B2 | 1/2021 | Choi et al. |
| 10,930,473 B2 | 2/2021 | Paukner et al. |
| 10,930,922 B2 | 2/2021 | Sun et al. |
| 10,937,632 B2 | 3/2021 | Stowell et al. |
| 10,943,744 B2 | 3/2021 | Sungail et al. |
| 10,944,093 B2 | 3/2021 | Paz et al. |
| 10,950,856 B2 | 3/2021 | Park et al. |
| 10,964,938 B2 | 3/2021 | Rojeski |
| 10,987,735 B2 | 4/2021 | Hadidi et al. |
| 10,998,552 B2 | 5/2021 | Lanning et al. |
| 11,011,388 B2 | 5/2021 | Eason et al. |
| 11,031,641 B2 | 6/2021 | Gupta et al. |
| 11,050,061 B2 | 6/2021 | Kim et al. |
| 11,072,533 B2 | 7/2021 | Shevchenko et al. |
| 11,077,497 B2 | 8/2021 | Motchenbacher et al. |
| 11,077,524 B2 | 8/2021 | Smathers et al. |
| 11,108,050 B2 | 8/2021 | Kim et al. |
| 11,116,000 B2 | 9/2021 | Sandberg et al. |
| 11,130,175 B2 | 9/2021 | Parrish et al. |
| 11,130,994 B2 | 9/2021 | Shachar et al. |
| 11,133,495 B2 | 9/2021 | Gazda et al. |
| 11,148,202 B2 | 10/2021 | Hadidi et al. |
| 11,167,556 B2 | 11/2021 | Shimada et al. |
| 11,170,753 B2 | 11/2021 | Nomura et al. |
| 11,171,322 B2 | 11/2021 | Seol et al. |
| 11,183,682 B2 | 11/2021 | Sunkara et al. |
| 11,193,142 B2 | 12/2021 | Angelidaki et al. |
| 11,196,045 B2 | 12/2021 | Dadheech et al. |
| 11,219,884 B2 | 1/2022 | Takeda et al. |
| 11,244,614 B2 | 2/2022 | He et al. |
| 11,245,065 B1 | 2/2022 | Ouderkirk et al. |
| 11,245,109 B2 | 2/2022 | Tzeng et al. |
| 11,246,961 B2 | 2/2022 | Wang et al. |
| 11,254,585 B2 | 2/2022 | Ekman et al. |
| 11,273,322 B2 | 3/2022 | Zanata et al. |
| 11,273,491 B2 | 3/2022 | Barnes et al. |
| 11,299,397 B2 | 4/2022 | Lanning et al. |
| 11,311,937 B2 | 4/2022 | Hadidi et al. |
| 11,311,938 B2 | 4/2022 | Badwe et al. |
| 11,319,537 B2 | 5/2022 | Dames et al. |
| 11,333,183 B2 | 5/2022 | Desai et al. |
| 11,335,911 B2 | 5/2022 | Lanning et al. |
| 11,350,680 B2 | 6/2022 | Rutkoski et al. |
| 11,380,521 B2 | 7/2022 | Anzelmo et al. |
| 11,411,253 B2 | 8/2022 | Busacca et al. |
| 11,439,206 B2 | 9/2022 | Santos |
| 11,442,000 B2 | 9/2022 | Vaez-Iravani et al. |
| 11,461,298 B1 | 10/2022 | Shemmer et al. |
| 11,465,201 B2 | 10/2022 | Barnes et al. |
| 11,471,941 B2 | 10/2022 | Barnes et al. |
| 11,477,665 B2 | 10/2022 | Franke et al. |
| 11,577,314 B2 | 2/2023 | Hadidi et al. |
| 11,590,568 B2 | 2/2023 | Badwe et al. |
| 11,611,130 B2 | 3/2023 | Wrobel et al. |
| 11,633,785 B2 | 4/2023 | Badwe et al. |
| 11,654,483 B2 | 5/2023 | Larouche et al. |
| 11,717,886 B2 | 8/2023 | Badwe et al. |
| 11,839,919 B2 | 12/2023 | Hadidi et al. |
| 11,855,278 B2 | 12/2023 | Holman et al. |
| 11,919,071 B2 | 3/2024 | Badwe et al. |
| 11,923,176 B2 | 3/2024 | Stowell et al. |
| 11,963,287 B2 | 4/2024 | Shang et al. |
| 2001/0016283 A1 | 8/2001 | Shiraishi et al. |
| 2001/0021740 A1 | 9/2001 | Lodyga et al. |
| 2002/0054912 A1 | 5/2002 | Kim et al. |
| 2002/0112794 A1 | 8/2002 | Sethuram et al. |
| 2003/0024806 A1 | 2/2003 | Foret |
| 2003/0027021 A1 | 2/2003 | Sharivker et al. |
| 2003/0070620 A1 | 4/2003 | Cooperberg et al. |
| 2003/0077398 A1 | 4/2003 | Strutt et al. |
| 2003/0129497 A1 | 7/2003 | Yamamoto et al. |
| 2003/0172772 A1 | 9/2003 | Sethuram et al. |
| 2003/0186128 A1 | 10/2003 | Singh et al. |
| 2003/0207978 A1 | 11/2003 | Yadav et al. |
| 2004/0013941 A1 | 1/2004 | Kobayashi et al. |
| 2004/0045807 A1 | 3/2004 | Sarkas et al. |
| 2004/0060387 A1 | 4/2004 | Tanner-Jones |
| 2004/0123699 A1 | 7/2004 | Liao et al. |
| 2004/0247522 A1 | 12/2004 | Mills |
| 2005/0002849 A1 | 1/2005 | Mitsui et al. |
| 2005/0005844 A1 | 1/2005 | Kitagawa et al. |
| 2005/0025698 A1 | 2/2005 | Talbot et al. |
| 2005/0072496 A1 | 4/2005 | Hwang et al. |
| 2005/0163696 A1 | 7/2005 | Uhm et al. |
| 2005/0202173 A1 | 9/2005 | Mills |
| 2005/0242070 A1 | 11/2005 | Hammer |
| 2005/0260786 A1 | 11/2005 | Yoshikawa et al. |
| 2006/0040168 A1 | 2/2006 | Sridhar |
| 2006/0141153 A1 | 6/2006 | Kubota et al. |
| 2006/0145124 A1 | 7/2006 | Hsiao et al. |
| 2006/0291827 A1 | 12/2006 | Suib et al. |
| 2007/0077350 A1 | 4/2007 | Hohenthanner et al. |
| 2007/0089860 A1 | 4/2007 | Hou et al. |
| 2007/0092432 A1 | 4/2007 | Prud et al. |
| 2007/0209758 A1 | 9/2007 | Sompalli et al. |
| 2007/0221635 A1 | 9/2007 | Boulos et al. |
| 2007/0259768 A1 | 11/2007 | Kear et al. |
| 2008/0029485 A1 | 2/2008 | Kelley et al. |
| 2008/0055594 A1 | 3/2008 | Hadidi et al. |
| 2008/0182114 A1 | 7/2008 | Kim et al. |
| 2008/0220244 A1 | 9/2008 | Wai et al. |
| 2008/0286490 A1 | 11/2008 | Bogdanoff et al. |
| 2008/0296268 A1 | 12/2008 | Mike et al. |
| 2008/0305025 A1 | 12/2008 | Vitner et al. |
| 2009/0074655 A1 | 3/2009 | Suciu |
| 2009/0093553 A1 | 4/2009 | Kleine et al. |
| 2009/0155689 A1 | 6/2009 | Zaghib et al. |
| 2009/0196801 A1 | 8/2009 | Mills |
| 2009/0202869 A1 | 8/2009 | Sawaki et al. |
| 2009/0246398 A1 | 10/2009 | Kurahashi et al. |
| 2009/0258255 A1 | 10/2009 | Terashima et al. |
| 2009/0266487 A1 | 10/2009 | Tian et al. |
| 2009/0278556 A1 | 11/2009 | Man et al. |
| 2009/0304941 A1 | 12/2009 | McLean |
| 2009/0305132 A1 | 12/2009 | Gauthier et al. |
| 2010/0007162 A1 | 1/2010 | Han et al. |
| 2010/0032640 A1 | 2/2010 | Xu |
| 2010/0096362 A1 | 4/2010 | Hirayama et al. |
| 2010/0176524 A1 | 7/2010 | Burgess et al. |
| 2010/0219062 A1 | 9/2010 | Leon Sanchez |
| 2011/0005461 A1 | 1/2011 | Vandermeulen |
| 2011/0006254 A1 | 1/2011 | Richard et al. |
| 2012/0015284 A1 | 1/2012 | Merzougui et al. |
| 2012/0027955 A1 | 2/2012 | Sunkara et al. |
| 2012/0034135 A1 | 2/2012 | Risby |
| 2012/0048064 A1 | 3/2012 | Kasper et al. |
| 2012/0051962 A1 | 3/2012 | Imam et al. |
| 2012/0074342 A1 | 3/2012 | Kim et al. |
| 2012/0100438 A1 | 4/2012 | Fasching et al. |
| 2012/0107525 A1 | 5/2012 | Ohmae |
| 2012/0112379 A1 | 5/2012 | Beppu et al. |
| 2012/0122017 A1 | 5/2012 | Mills |
| 2012/0224175 A1 | 9/2012 | Minghetti |
| 2012/0230860 A1 | 9/2012 | Ward-Close et al. |
| 2012/0240726 A1 | 9/2012 | Kim et al. |
| 2012/0294919 A1 | 11/2012 | Jaynes et al. |
| 2013/0032753 A1 | 2/2013 | Yamamoto et al. |
| 2013/0043119 A1 | 2/2013 | Xia et al. |
| 2013/0071284 A1 | 3/2013 | Kano et al. |
| 2013/0075390 A1 | 3/2013 | Ashida |
| 2013/0078508 A1 | 3/2013 | Tolbert et al. |
| 2013/0084474 A1 | 4/2013 | Mills |
| 2013/0087285 A1 | 4/2013 | Kofuji et al. |
| 2013/0341185 A1 | 12/2013 | Collaert et al. |
| 2014/0048516 A1 | 2/2014 | Gorodetsky et al. |

(56) References Cited

U.S. PATENT DOCUMENTS

| | | |
|---|---|---|
| 2014/0202286 A1 | 7/2014 | Yokoyama et al. |
| 2014/0271843 A1 | 9/2014 | Ma et al. |
| 2014/0272430 A1 | 9/2014 | Kalayaraman |
| 2014/0322632 A1 | 10/2014 | Sugimoto et al. |
| 2014/0373344 A1 | 12/2014 | Takada et al. |
| 2015/0000844 A1 | 1/2015 | Woo |
| 2015/0007773 A1 | 1/2015 | Toyoshima et al. |
| 2015/0101454 A1 | 4/2015 | Shimizu et al. |
| 2015/0167143 A1 | 6/2015 | Luce et al. |
| 2015/0171455 A1 | 6/2015 | Mills |
| 2015/0255767 A1 | 9/2015 | Aetukuri et al. |
| 2015/0259220 A1 | 9/2015 | Rosocha et al. |
| 2015/0270106 A1 | 9/2015 | Kobayashi et al. |
| 2015/0333307 A1 | 11/2015 | Thokchom et al. |
| 2015/0342491 A1 | 12/2015 | Marecki et al. |
| 2015/0351652 A1 | 12/2015 | Marecki et al. |
| 2016/0028088 A1 | 1/2016 | Romeo et al. |
| 2016/0030359 A1 | 2/2016 | Ma et al. |
| 2016/0045841 A1 | 2/2016 | Kaplan et al. |
| 2016/0152480 A1 | 6/2016 | Jang et al. |
| 2016/0172163 A1 | 6/2016 | Kaneko et al. |
| 2016/0189933 A1 | 6/2016 | Kobayashi et al. |
| 2016/0197341 A1 | 7/2016 | Lu et al. |
| 2016/0209043 A1 | 7/2016 | Gao et al. |
| 2016/0217979 A1 | 7/2016 | Kim et al. |
| 2016/0254540 A1 | 9/2016 | Lee et al. |
| 2016/0284519 A1 | 9/2016 | Kobayashi et al. |
| 2016/0285090 A1 | 9/2016 | Ozkan et al. |
| 2016/0287113 A1 | 10/2016 | Hebert et al. |
| 2016/0293346 A1 | 10/2016 | Xiong et al. |
| 2016/0308244 A1 | 10/2016 | Badding et al. |
| 2016/0332232 A1 | 11/2016 | Forbes et al. |
| 2016/0351910 A1 | 12/2016 | Albano et al. |
| 2016/0358757 A1 | 12/2016 | Ikeda et al. |
| 2017/0009328 A1 | 1/2017 | Germann et al. |
| 2017/0070180 A1 | 3/2017 | Mills |
| 2017/0113935 A1 | 4/2017 | Pennington et al. |
| 2017/0120339 A1 | 5/2017 | Aslund |
| 2017/0125842 A1 | 5/2017 | Meguro et al. |
| 2017/0151609 A1 | 6/2017 | Elsen et al. |
| 2017/0176977 A1 | 6/2017 | Huang et al. |
| 2017/0179477 A1 | 6/2017 | Walters et al. |
| 2017/0209922 A1 | 7/2017 | Kato et al. |
| 2017/0338464 A1 | 11/2017 | Fasching et al. |
| 2017/0368604 A1 | 12/2017 | Wilkinson |
| 2017/0373344 A1 | 12/2017 | Hadidi et al. |
| 2018/0022928 A1 | 1/2018 | Blush |
| 2018/0025794 A1 | 1/2018 | Lahoda et al. |
| 2018/0083264 A1 | 3/2018 | Soppe |
| 2018/0104745 A1 | 4/2018 | L'Esperance et al. |
| 2018/0114677 A1 | 4/2018 | Komatsu et al. |
| 2018/0130638 A1 | 5/2018 | Ahmad et al. |
| 2018/0134629 A1 | 5/2018 | Kolios et al. |
| 2018/0138018 A1 | 5/2018 | Voronin et al. |
| 2018/0159178 A1 | 6/2018 | Weisenstein et al. |
| 2018/0169763 A1 | 6/2018 | Dorval et al. |
| 2018/0214956 A1 | 8/2018 | Larouche et al. |
| 2018/0218883 A1 | 8/2018 | Iwao |
| 2018/0226229 A1 | 8/2018 | Stowell et al. |
| 2018/0241956 A1 | 8/2018 | Suzuki |
| 2018/0248175 A1 | 8/2018 | Ghezelbash et al. |
| 2018/0277826 A1 | 9/2018 | Gayden et al. |
| 2018/0277849 A1 | 9/2018 | Gayden |
| 2018/0294143 A1 | 10/2018 | Chua et al. |
| 2018/0346344 A1 | 12/2018 | Chen et al. |
| 2018/0353643 A1 | 12/2018 | Ma et al. |
| 2018/0363104 A1 | 12/2018 | Fujieda et al. |
| 2018/0366707 A1 | 12/2018 | Johnson et al. |
| 2018/0375149 A1 | 12/2018 | Beck et al. |
| 2019/0001416 A1 | 1/2019 | Larouche et al. |
| 2019/0046946 A1* | 2/2019 | Strohm ............ B01J 19/088 |
| 2019/0061005 A1 | 2/2019 | Kelkar |
| 2019/0069944 A1 | 3/2019 | Fischer |
| 2019/0084290 A1 | 3/2019 | Stoyanov et al. |
| 2019/0088993 A1 | 3/2019 | Ohta |
| 2019/0125842 A1 | 5/2019 | Grabowski |
| 2019/0127835 A1 | 5/2019 | Yang et al. |
| 2019/0157045 A1 | 5/2019 | Meloni |
| 2019/0160528 A1 | 5/2019 | Mcgee et al. |
| 2019/0165413 A1 | 5/2019 | Furusawa |
| 2019/0173130 A1 | 6/2019 | Schuhmacher et al. |
| 2019/0193151 A1 | 6/2019 | Okumura et al. |
| 2019/0218650 A1 | 7/2019 | Subramanian et al. |
| 2019/0267215 A1 | 8/2019 | Rats et al. |
| 2019/0271068 A1 | 9/2019 | Sungail et al. |
| 2019/0292441 A1 | 9/2019 | Hill et al. |
| 2019/0334206 A1 | 10/2019 | Sastry et al. |
| 2019/0341650 A9 | 11/2019 | Lanning et al. |
| 2019/0348202 A1 | 11/2019 | Sachdev et al. |
| 2019/0362936 A1 | 11/2019 | Van Den Berg et al. |
| 2019/0389734 A1 | 12/2019 | Dietz et al. |
| 2020/0067128 A1 | 2/2020 | Chmiola et al. |
| 2020/0136176 A1 | 4/2020 | Chen |
| 2020/0149146 A1 | 5/2020 | Chen et al. |
| 2020/0153037 A1 | 5/2020 | Renna et al. |
| 2020/0187607 A1 | 6/2020 | Law |
| 2020/0198977 A1 | 6/2020 | Hof et al. |
| 2020/0203706 A1 | 6/2020 | Holman et al. |
| 2020/0207668 A1 | 7/2020 | Cavalli et al. |
| 2020/0220222 A1 | 7/2020 | Watarai et al. |
| 2020/0223704 A1 | 7/2020 | Neale et al. |
| 2020/0227728 A1 | 7/2020 | Huang et al. |
| 2020/0254432 A1 | 8/2020 | Shirman et al. |
| 2020/0276638 A1 | 9/2020 | King et al. |
| 2020/0288561 A1 | 9/2020 | Huh |
| 2020/0314991 A1 | 10/2020 | Duanmu et al. |
| 2020/0325574 A1 | 10/2020 | Tseng et al. |
| 2020/0335754 A1 | 10/2020 | Ramasubramanian et al. |
| 2020/0335781 A1 | 10/2020 | Oshita et al. |
| 2020/0350565 A1 | 11/2020 | Oshita et al. |
| 2020/0358093 A1 | 11/2020 | Oshita et al. |
| 2020/0358096 A1 | 11/2020 | Paulsen et al. |
| 2020/0381217 A1 | 12/2020 | Kraus et al. |
| 2020/0388857 A1 | 12/2020 | Sunkara et al. |
| 2020/0391295 A1 | 12/2020 | Dorval et al. |
| 2020/0395607 A1 | 12/2020 | Tzeng |
| 2020/0402768 A1* | 12/2020 | Stowell ............ H01J 37/32229 |
| 2020/0403236 A1 | 12/2020 | Colwell |
| 2020/0407858 A1 | 12/2020 | Sano et al. |
| 2021/0002759 A1 | 1/2021 | Zhang et al. |
| 2021/0024358 A1 | 1/2021 | Chae et al. |
| 2021/0047186 A1 | 2/2021 | Ifuku et al. |
| 2021/0057191 A1 | 2/2021 | Stowell et al. |
| 2021/0075000 A1 | 3/2021 | Holman et al. |
| 2021/0085468 A1 | 3/2021 | Ryd et al. |
| 2021/0098826 A1 | 4/2021 | Chung et al. |
| 2021/0139331 A1 | 5/2021 | Kang et al. |
| 2021/0187614 A1 | 6/2021 | Tsubota et al. |
| 2021/0212905 A1 | 7/2021 | Rosiwal et al. |
| 2021/0226302 A1 | 7/2021 | Lanning et al. |
| 2021/0253430 A1 | 8/2021 | Zaplotnik et al. |
| 2021/0273217 A1 | 9/2021 | Park et al. |
| 2021/0273292 A1 | 9/2021 | Yun et al. |
| 2021/0276094 A1 | 9/2021 | Sobu et al. |
| 2021/0296731 A1 | 9/2021 | Wrobel et al. |
| 2021/0310110 A1 | 10/2021 | Stowell et al. |
| 2021/0339313 A1 | 11/2021 | Motchenbacher et al. |
| 2021/0344059 A1 | 11/2021 | Ekman et al. |
| 2021/0367264 A1 | 11/2021 | Hadidi et al. |
| 2022/0041457 A1 | 2/2022 | Pullen et al. |
| 2022/0063012 A1 | 3/2022 | Murata et al. |
| 2022/0095445 A1 | 3/2022 | Shang et al. |
| 2022/0127145 A1 | 4/2022 | Ding et al. |
| 2022/0134430 A1 | 5/2022 | Larouche et al. |
| 2022/0134431 A1 | 5/2022 | Badwe et al. |
| 2022/0143693 A1 | 5/2022 | Larouche et al. |
| 2022/0185730 A1 | 6/2022 | Skoptsov et al. |
| 2022/0209298 A1 | 6/2022 | Kim et al. |
| 2022/0223379 A1 | 7/2022 | Holman et al. |
| 2022/0228288 A1 | 7/2022 | Holman et al. |
| 2022/0267216 A1 | 8/2022 | Holman et al. |
| 2022/0314325 A1 | 10/2022 | Badwe |
| 2022/0324022 A1 | 10/2022 | Badwe |
| 2022/0352549 A1 | 11/2022 | Kim et al. |

(56) References Cited

U.S. PATENT DOCUMENTS

| | | |
|---|---|---|
| 2023/0001375 A1 | 1/2023 | Kozlowski et al. |
| 2023/0001376 A1 | 1/2023 | Kozlowski et al. |
| 2023/0025008 A1 | 1/2023 | Lee et al. |
| 2023/0032362 A1 | 2/2023 | Holman et al. |
| 2023/0042099 A1 | 2/2023 | Wada et al. |
| 2023/0069456 A1 | 3/2023 | Stowell et al. |
| 2023/0074143 A1 | 3/2023 | Stowell et al. |
| 2023/0100863 A1 | 3/2023 | Lianto et al. |
| 2023/0143022 A1 | 5/2023 | Mills |
| 2023/0144075 A1 | 5/2023 | Badwe et al. |
| 2023/0211407 A1 | 7/2023 | Hadidi |
| 2023/0219134 A1 | 7/2023 | Houshmand et al. |
| 2023/0245896 A1 | 8/2023 | Gupta et al. |
| 2023/0247751 A1 | 8/2023 | Kozlowski et al. |
| 2023/0298885 A1 | 9/2023 | Borude et al. |
| 2023/0330747 A1 | 10/2023 | Barnes et al. |
| 2023/0330748 A1 | 10/2023 | Badwe et al. |
| 2023/0377848 A1 | 11/2023 | Holman et al. |
| 2023/0395889 A1 | 12/2023 | Yang et al. |
| 2023/0411123 A1 | 12/2023 | Kozlowski et al. |
| 2024/0017322 A1 | 1/2024 | Badwe et al. |
| 2024/0057245 A1 | 2/2024 | Kozlowski et al. |
| 2024/0071725 A1 | 2/2024 | Kozlowsk et al. |
| 2024/0088369 A1 | 3/2024 | Holman et al. |
| 2024/0088467 A1 | 3/2024 | Liao et al. |

FOREIGN PATENT DOCUMENTS

| | | |
|---|---|---|
| AU | 2020220233 A1 | 9/2021 |
| CA | 2947531 A1 | 11/2015 |
| CN | 1188073 A | 7/1998 |
| CN | 1653869 A | 8/2005 |
| CN | 1675785 A | 9/2005 |
| CN | 1967911 A | 5/2007 |
| CN | 101191204 A | 6/2008 |
| CN | 101391307 A | 3/2009 |
| CN | 101728509 A | 6/2010 |
| CN | 101804962 A | 8/2010 |
| CN | 101716686 B | 2/2011 |
| CN | 102179521 A | 9/2011 |
| CN | 102328961 A | 1/2012 |
| CN | 102394290 A | 3/2012 |
| CN | 102412377 A | 4/2012 |
| CN | 102427130 A | 4/2012 |
| CN | 102664273 A | 9/2012 |
| CN | 102723502 A | 10/2012 |
| CN | 102867940 A | 1/2013 |
| CN | 102983312 A | 3/2013 |
| CN | 103121105 A | 5/2013 |
| CN | 103402921 A | 11/2013 |
| CN | 102554242 B | 12/2013 |
| CN | 103456926 A | 12/2013 |
| CN | 103682372 A | 3/2014 |
| CN | 103682383 A | 3/2014 |
| CN | 103700815 A | 4/2014 |
| CN | 103874538 A | 6/2014 |
| CN | 103956520 A | 7/2014 |
| CN | 104064736 A | 9/2014 |
| CN | 104084592 A | 10/2014 |
| CN | 104209526 A | 12/2014 |
| CN | 104218213 A | 12/2014 |
| CN | 204156003 U | 2/2015 |
| CN | 104485452 A | 4/2015 |
| CN | 104752734 A | 7/2015 |
| CN | 104772473 A | 7/2015 |
| CN | 103515590 B | 9/2015 |
| CN | 105514373 A | 4/2016 |
| CN | 106001597 A | 10/2016 |
| CN | 106044777 A | 10/2016 |
| CN | 106159316 A | 11/2016 |
| CN | 106216703 A | 12/2016 |
| CN | 106450146 A | 2/2017 |
| CN | 106493350 A | 3/2017 |
| CN | 206040854 U | 3/2017 |
| CN | 106684387 A | 5/2017 |
| CN | 106756417 A | 5/2017 |
| CN | 106784692 A | 5/2017 |
| CN | 107093732 A | 8/2017 |
| CN | 107170973 A | 9/2017 |
| CN | 107579241 A | 1/2018 |
| CN | 107931622 A | 4/2018 |
| CN | 108134104 A | 6/2018 |
| CN | 108145170 A | 6/2018 |
| CN | 108217612 A | 6/2018 |
| CN | 108649190 A | 10/2018 |
| CN | 108666563 A | 10/2018 |
| CN | 108672709 A | 10/2018 |
| CN | 108878862 A | 11/2018 |
| CN | 108907210 A | 11/2018 |
| CN | 108933239 A | 12/2018 |
| CN | 108963239 A | 12/2018 |
| CN | 109167070 A | 1/2019 |
| CN | 109301212 A | 2/2019 |
| CN | 109616622 A | 4/2019 |
| CN | 109742320 A | 5/2019 |
| CN | 109808049 A | 5/2019 |
| CN | 109888233 A | 6/2019 |
| CN | 110153434 A | 8/2019 |
| CN | 110218897 A | 9/2019 |
| CN | 110299516 A | 10/2019 |
| CN | 110451496 A | 11/2019 |
| CN | 110790263 A | 2/2020 |
| CN | 110993908 A | 4/2020 |
| CN | 111099577 A | 5/2020 |
| CN | 111342163 A | 6/2020 |
| CN | 111370751 A | 7/2020 |
| CN | 111403701 A | 7/2020 |
| CN | 111515391 A | 8/2020 |
| CN | 111970807 A | 11/2020 |
| CN | 112259740 A | 1/2021 |
| CN | 112331947 A | 2/2021 |
| CN | 112397706 A | 2/2021 |
| CN | 112421006 A | 2/2021 |
| CN | 112421048 A | 2/2021 |
| CN | 112447977 A | 3/2021 |
| CN | 112768709 A | 5/2021 |
| CN | 112768710 A | 5/2021 |
| CN | 112768711 A | 5/2021 |
| CN | 112864453 A | 5/2021 |
| CN | 113097487 A | 7/2021 |
| CN | 113104838 A | 7/2021 |
| CN | 113764688 A | 12/2021 |
| CN | 113871581 A | 12/2021 |
| CN | 113942996 A | 1/2022 |
| CN | 114388822 A | 4/2022 |
| CN | 114744315 A | 7/2022 |
| CN | 114824297 A | 7/2022 |
| CN | 115353098 A | 11/2022 |
| CN | 115394976 A | 11/2022 |
| DE | 10335355 A1 | 11/2004 |
| DE | 102009033251 A1 | 9/2010 |
| DE | 102010006440 A1 | 8/2011 |
| DE | 102011109137 A1 | 2/2013 |
| DE | 602004043916 T2 | 11/2013 |
| DE | 602004044163 T2 | 1/2014 |
| DE | 102018132896 A1 | 6/2020 |
| EP | 0256233 A2 | 2/1988 |
| EP | 2292557 A1 | 3/2011 |
| EP | 3143838 A1 | 3/2017 |
| EP | 3474978 A1 | 5/2019 |
| FR | 2525122 A1 | 10/1983 |
| FR | 2591412 A1 | 6/1987 |
| GB | 2595745 A | 12/2021 |
| GB | 2620597 A | 1/2024 |
| IN | 311758 B | 4/2019 |
| IN | 319669 B | 9/2019 |
| IN | 202011017775 | 10/2021 |
| JP | 63-243212 | 10/1988 |
| JP | 10-172564 A | 6/1998 |
| JP | 10-296446 A | 11/1998 |
| JP | 11-064556 A | 3/1999 |
| JP | 2001-064703 A | 3/2001 |
| JP | 2001-504753 A | 4/2001 |
| JP | 2001-348296 A | 12/2001 |

(56) References Cited

FOREIGN PATENT DOCUMENTS

| | | |
|---|---|---|
| JP | 2002-249836 A | 9/2002 |
| JP | 2002-332531 A | 11/2002 |
| JP | 2004-034014 A | 2/2004 |
| JP | 2004-505761 A | 2/2004 |
| JP | 2004-193115 A | 7/2004 |
| JP | 2004-232084 A | 8/2004 |
| JP | 2004-311297 A | 11/2004 |
| JP | 2004-340414 A | 12/2004 |
| JP | 2004-362895 A | 12/2004 |
| JP | 2005-015282 A | 1/2005 |
| JP | 2005-072015 A | 3/2005 |
| JP | 2005-076052 A | 3/2005 |
| JP | 2005-135755 A | 5/2005 |
| JP | 2005-187295 A | 7/2005 |
| JP | 2005-222956 A | 8/2005 |
| JP | 2005-272284 A | 10/2005 |
| JP | 2006-040722 A | 2/2006 |
| JP | 2007-113120 A | 5/2007 |
| JP | 2007-138287 A | 6/2007 |
| JP | 2007-149513 A | 6/2007 |
| JP | 2007-238402 A | 9/2007 |
| JP | 2008-230905 A | 10/2008 |
| JP | 2008-243447 A | 10/2008 |
| JP | 2009-187754 A | 8/2009 |
| JP | 2010-024506 A | 2/2010 |
| JP | 2010-097914 A | 4/2010 |
| JP | 2011-108406 A | 6/2011 |
| JP | 2011-222323 A | 11/2011 |
| JP | 2011-258348 A | 12/2011 |
| JP | 2012-046393 A | 3/2012 |
| JP | 2012-151052 A | 8/2012 |
| JP | 2012-234788 A | 11/2012 |
| JP | 2013-062242 A | 4/2013 |
| JP | 2013-063539 A | 4/2013 |
| JP | 2013-069602 A | 4/2013 |
| JP | 2013-076130 A | 4/2013 |
| JP | 2015-048269 A | 3/2015 |
| JP | 2015-122218 A | 7/2015 |
| JP | 2016-029193 A | 3/2016 |
| JP | 2016-047961 A | 4/2016 |
| JP | 6103499 B2 | 3/2017 |
| JP | 2017-524628 A | 8/2017 |
| JP | 2018-141762 A | 9/2018 |
| JP | 2018-528328 A | 9/2018 |
| JP | 2018-190563 A | 11/2018 |
| JP | 2019-055898 A | 4/2019 |
| JP | 2019-516020 A | 6/2019 |
| JP | 2019-112699 A | 7/2019 |
| JP | 2019-520894 A | 7/2019 |
| JP | 2020-121898 A | 8/2020 |
| JP | 2021-061089 A | 4/2021 |
| JP | 2021-061090 A | 4/2021 |
| JP | 2021-116191 A | 8/2021 |
| JP | 2022-530649 A | 6/2022 |
| KR | 10-0582507 B1 | 5/2006 |
| KR | 10-2007-0076686 A | 7/2007 |
| KR | 10-2009-0070140 A | 7/2009 |
| KR | 10-1133094 B1 | 4/2012 |
| KR | 10-2014-0001813 U | 3/2014 |
| KR | 20-2014-0001813 U | 3/2014 |
| KR | 10-1684219 B1 | 12/2016 |
| KR | 10-2017-0039922 A | 4/2017 |
| KR | 10-2017-0045181 A | 4/2017 |
| KR | 10-2018-0001799 A | 1/2018 |
| KR | 10-2018-0035750 A | 4/2018 |
| KR | 10-1907912 B1 | 10/2018 |
| KR | 10-1907916 B1 | 10/2018 |
| KR | 10-1923466 B1 | 11/2018 |
| KR | 10-2101006 B1 | 4/2020 |
| KR | 10-2124946 B1 | 6/2020 |
| KR | 10-2020-0131751 A | 11/2020 |
| KR | 10-2021-0057253 A | 5/2021 |
| MY | PI2020003449 | 7/2019 |
| RU | 2744449 C1 | 3/2021 |
| TW | 521539 B | 2/2003 |
| TW | M303584 U | 12/2006 |
| TW | 200737342 A | 10/2007 |
| TW | 200823313 A | 6/2008 |
| TW | 1329143 B | 8/2010 |
| TW | 201112481 A | 4/2011 |
| TW | 201225389 A | 6/2012 |
| TW | 201310758 A | 3/2013 |
| TW | 201411922 A | 3/2014 |
| TW | 1593484 B | 8/2017 |
| TW | 202002723 A | 1/2020 |
| TW | 202033297 A | 9/2020 |
| WO | 03/77333 A1 | 9/2003 |
| WO | 2004/054017 A1 | 6/2004 |
| WO | 2004/089821 A1 | 10/2004 |
| WO | 2005/039752 A1 | 5/2005 |
| WO | 2006/100837 A1 | 9/2006 |
| WO | 2007/101174 A2 | 9/2007 |
| WO | 2010/095726 A1 | 8/2010 |
| WO | 2011/082596 A1 | 7/2011 |
| WO | 2011/090779 A2 | 7/2011 |
| WO | 2012/023858 A1 | 2/2012 |
| WO | 2012/114108 A1 | 8/2012 |
| WO | 2012/144424 A1 | 10/2012 |
| WO | 2012/162743 A1 | 12/2012 |
| WO | 2013/017217 A1 | 2/2013 |
| WO | 2014/011239 A2 | 1/2014 |
| WO | 2014/110604 A2 | 7/2014 |
| WO | 2014/153318 A1 | 9/2014 |
| WO | 2015/064633 A1 | 5/2015 |
| WO | 2015/174949 A1 | 11/2015 |
| WO | 2015/187389 A2 | 12/2015 |
| WO | 2015/193689 A1 | 12/2015 |
| WO | 2016/048862 A1 | 3/2016 |
| WO | 2016/082120 A1 | 6/2016 |
| WO | 2016/091957 A1 | 6/2016 |
| WO | 2017/074081 A1 | 5/2017 |
| WO | 2017/074084 A1 | 5/2017 |
| WO | 2017/080978 A1 | 5/2017 |
| WO | 2017/091543 A1 | 6/2017 |
| WO | 2017/106601 A8 | 7/2017 |
| WO | 2017/118955 A1 | 7/2017 |
| WO | 2017/130946 A1 | 8/2017 |
| WO | 2017/158349 A1 | 9/2017 |
| WO | 2017/177315 A1 | 10/2017 |
| WO | 2017/178841 A1 | 10/2017 |
| WO | 2017/196198 A2 | 11/2017 |
| WO | 2017/223482 A1 | 12/2017 |
| WO | 2018/133429 A1 | 7/2018 |
| WO | 2018/141082 A1 | 8/2018 |
| WO | 2018/145750 A1 | 8/2018 |
| WO | 2019/045923 A1 | 3/2019 |
| WO | 2019/052670 A1 | 3/2019 |
| WO | 2019/095039 A1 | 5/2019 |
| WO | 2019/124344 A1 | 6/2019 |
| WO | 2019/139773 A1 | 7/2019 |
| WO | 2019/178668 A1 | 9/2019 |
| WO | 2019/243870 A1 | 12/2019 |
| WO | 2019/246242 A1 | 12/2019 |
| WO | 2019/246257 A1 | 12/2019 |
| WO | 2020/009955 A1 | 1/2020 |
| WO | 2020/013667 A1 | 1/2020 |
| WO | 2020/041767 A1 | 2/2020 |
| WO | 2020/041775 A1 | 2/2020 |
| WO | 2020/091854 A1 | 5/2020 |
| WO | 2020/132343 A1 | 6/2020 |
| WO | 2020/223358 A1 | 11/2020 |
| WO | 2020/223374 A1 | 11/2020 |
| WO | 2021/029769 A1 | 2/2021 |
| WO | 2021/046249 A1 | 3/2021 |
| WO | 2021/085670 A1 | 5/2021 |
| WO | 2021/115596 A1 | 6/2021 |
| WO | 2021/118762 A1 | 6/2021 |
| WO | 2021/127132 A1 | 6/2021 |
| WO | 2021/159117 A1 | 8/2021 |
| WO | 2021/191281 A1 | 9/2021 |
| WO | 2021/245410 A1 | 12/2021 |
| WO | 2021/245411 A1 | 12/2021 |
| WO | 2021/263273 A1 | 12/2021 |
| WO | 2022/005999 A1 | 1/2022 |

(56) References Cited

FOREIGN PATENT DOCUMENTS

| | | |
|---|---|---|
| WO | 2022/032301 A1 | 2/2022 |
| WO | 2022/043701 A1 | 3/2022 |
| WO | 2022/043702 A1 | 3/2022 |
| WO | 2022/043704 A1 | 3/2022 |
| WO | 2022/043705 A1 | 3/2022 |
| WO | 2022/067303 A1 | 3/2022 |
| WO | 2022/075846 A1 | 4/2022 |
| WO | 2022/107907 A1 | 5/2022 |
| WO | 2022/133585 A1 | 6/2022 |
| WO | 2022/136699 A1 | 6/2022 |
| WO | 2022/150828 A1 | 7/2022 |
| WO | 2022/169659 A1 | 8/2022 |
| WO | 2022/261697 A1 | 12/2022 |
| WO | 2023/022492 A1 | 2/2023 |
| WO | 2023/023187 A1 | 2/2023 |

OTHER PUBLICATIONS

Sabat, K.C., "Hydrogen Plasma—Thermodynamics", Journal of Physics: Conference Series, 2019, International Conference on Applied Physics, Powder and Material Science, in 6 pages.

Schmidt-Ott, K., "Plasma-Reduction: Its Potential for Use in the Conservation of Metals", Proceedings of Metal 2004, Oct. 2004, pp. 235-246.

Singh, M., et al., "Effect of hydrogen concentration on graphene synthesis using microwave-driven plasma-mediated methane cracking", Carbon, vol. 143, Dec. 3, 2018, pp. 802-813.

Thierry, "Hydrogen (H2) Plasma", Thierry Corp., retrieved from internet on Feb. 15, 2024, in 2 pages. URL: https://www.thierry-corp.com/plasma-knowledgebase/hydrogen-h2-plasma.

Wang, X. X., et al., "Carbon nanocages: A new support material for Pt catalyst with remarkably high durability", Scientific reports, vol. 4, 2014, 11 pages.

Wu, Q., et al., "Carbon-Based Nanocages: A New Platform for Advanced Energy Storage and Conversion", Adv. Mater., 2019, 23 pages.

Zhao Jing et al., Introduction to Materials Science, China Light Industry Press, Jun. 2013, 2nd edition, 1st printing, p. 61.

Kim, K. S., et al., "Synthesis of single-walled carbon nanotubes by induction thermal plasma", Nano Research, 2009, vol. 2, No. 10, pp. 800-817.

Kim, S. et al., "Thermodynamic Evaluation of Oxygen Behavior in Ti Powder Deoxidized by Ca Reductant", Met. Mater. Int., 2016, vol. 22, pp. 658-662.

Ko, M. et al., "Challenges in Accommodating Volume Change of Si Anodes for Li-Ion Batteries", Chem Electro Chem, Aug. 2015, vol. 2, pp. 1645-1651. URL: https://doi.org/10.1002/celc.201500254.

Kotlyarov, V. I. et al., "Production of Spherical Powders on the Basis of Group IV Metals for Additive Manufacturing", Inorganic Materials: Applied Research, Pleiades Publishing, May 2017, vol. 8, No. 3, pp. 452-458.

Kumal, R. R., et al., "Microwave Plasma Formation of Nanographene and Graphitic Carbon Black", C—Journal of Carbon Research, 2020, vol. 6, No. 4, 10 pages.

Laine, R. M. et al., "Making nanosized oxide powders from precursors by flame spray pyrolysis", Key Engineering Materials, Jan. 1999, vol. 159-160, pp. 17-24.

Lee, D. H., et al., "Comparative Study of Methane Activation Process by Different Plasma Sources", Plasma Chem. Plasma Process., vol. 33, No. 4, 2013, pp. 647-661.

Lee, D. H., et al., "Mapping Plasma Chemistry in Hydrocarbon Fuel Processing Processes", Plasma Chem. Plasma Process., vol. 33, No. 1, 2013, pp. 249-269.

Li, L. et al., "Spheroidization of silica powders by radio frequency inductively coupled plasma with Ar—H2 and Ar—N2 as the sheath gases at atmospheric pressure", International Journal of Minerals, Metallurgy, and Materials, Sep. 2017, vol. 24(9), pp. 1067-1074.

Li, X. et al., "Mesoporous silicon sponge as an anti-pulverization structure for high-performance lithium-ion battery anodes", Nature Communications, Jul. 2014, vol. 5, Article No. 4105, in 7 pages. URL: httDs://doi.orq/10.1038/ncomms5105.

Li, Z. et al., "Strong and Ductile Non-Equicaloric High-Entropy Alloys: Design, Processing, Microstructure, and Mechanical Properties", The Journal of the Minerals, Metals & Materials Society, Aug. 2017, vol. 69(1), pp. 2099-2106. URL: https://doi.org/10.1007/s11837-017-2540-2.

Lin et al., A low temperature molten salt process for aluminothermic reduction of silicon oxides to crystalline Si for Li-ion batteries, Energy Environ. Sci., 2015, 8, 3187 (Year: 2015).

Lin, M., "Gas Quenching with Air Products' Rapid Gas Quenching Gas Mixture", Air Products, Dec. 31, 2007, in 4 pages. URL: hllps://www.airproducts.co.uk/-/media/airproducls/liles/en/330/330-07-085-us-gas-quenching-wilh-air-products-rapid-Jas-quenching-gas-mixture.pdf.

Liu, Y., et al., "Advances of microwave plasma-enhanced chemical vapor deposition in fabrication of carbon nanotubes: a review", J Mater Sci., vol. 55, 2021, pp. 12559-12583.

Liu, Z., et al., "Synthesis and characterization of LiNi1-x-yCoxMnyO2 as the cathode materials of secondary lithium batteries", Journal of Power Sources, vol. 81-82, Sep. 1999, pp. 416-419.

Majewksi, T., "Investigation of W-Re-Ni heavy alloys produced from plasma spheroidized powders", Solid State Phenomena, Mar. 2013, vol. 199, pp. 448-453.

Miller et al., The reduction of silica with carbon and silicon carbide, Journal of the American Ceramic Society, 1978, 62 (Year: 1978).

Moisan, M. et al., "Waveguide-Based Single and Multiple Nozzle Plasma Torches: the Tiago Concept", Plasma Sources Science and Technology, Jun. 2001, vol. 10, pp. 387-394.

Moldover, M. R. et al., "Measurement of the Universal Gas Constant R Using a Spherical Acoustic Resonator", Physical Review Letters, Jan. 1988, vol. 60(4), pp. 249-252.

Muoio, C. et al., "Phase Homogeneity in Y2O3—MgO Nanocomposites Synthesized by Thermal Decomposition of Nitrate Precursors with Ammonium Acetate Additions" J. Am. Ceram. Soc., 94[12] 4207-4217, 2011.

Murugan et al. "Nanostructured a/β-tungsten by reduction of WO3 under microwave plasma", Int. Journal of Refractory Metals and Hard Materials 29 (2011) 128-133. (Year: 2011).

Nichols, F. A., "On the spheroidization of rod-shaped particles of finite length", Journal of Materials Science, Jun. 1976, vol. 11, pp. 1077-1082.

Nyutu, E. et al., "Ultrasonic Nozzle Spray in Situ Mixing and Microwave-Assisted Preparation of Nanocrystalline Spinel Metal Oxides: Nickel Ferrite and Zinc Aluminate", Journal of Physical Chemistry C, Feb. 1, 2008, vol. 112, No. 5, pp. 1407-1414.

Ohta, R. et al., "Effect of PS-PVD production throughput on Si nanoparticles for negative electrode of lithium ion batteries", Journal of Physics D: Applied Physics, Feb. 2018, vol. 51(1), in 7 pages.

Olsvik, O., et al., "Thermal Coupling of Methane—A Comparison Between Kinetic Model Data and Experimental Data", Thermochimica Acta., vol. 232, No. 1, 1994, pp. 155-169.

Or, T. et al., "Recycling of mixed cathode lithium-ion batteries for electric vehicles: Current status and future outlook", Carbon Energy, Jan. 2020, vol. 2, pp. 6-43. URL: https://doi.org/10.1002/cey2.29.

Park et al.. "Preparation of spherical WTaMoNbV refractory high entropy alloy powder by inductively-coupled thermal plasma", Materials Letters 255 (2019) 126513 (Year: 2019).

Popescu et al.. "New TiZrNbTaFe high entropy alloy used for medical applications" IOP Conference Series: Materials Science and Engineering 400. Mod Tech 2018 (2018), 9 pages.

Pulsation Reactors—Thermal Processing for Extraordinary Material Properties, retrieved from https://www.ibu-tec.com/facilities/pulsation-reactors/, retrieved on Mar. 18, 2023, pp. 5.

Reig, L. et al., "Microstructure and Mechanical Behavior of Porous Ti—6Al—4V Processed by Spherical Powder Sintering", Materials, Oct. 23, 2013, vol. 6, pp. 4868-4878.

Sastry, S.M.L. et al., "Rapid Solidification Processing of Titanium Alloys", Journal of Metals (JOM), Sep. 1983, vol. 35, pp. 21-28.

Savage, S. J. et al., "Production of rapidly solidified metals and alloys", Journal of Metals (JOM), Apr. 1984, vol. 36, pp. 20-33.

(56) References Cited

OTHER PUBLICATIONS

Seehra, M. S., et al., "Correlation between X-ray diffraction and Raman spectra of 16 commercial graphene-based materials and their resulting classification", Carbon N Y., 2017, vol. 111, pp. 380-384.

Sheng, Y. et al., "Preparation of Micro-spherical Titanium Powder by RF Plasma", Rare Metal Materials and Engineering, Jun. 2013, vol. 42, No. 6, pp. 1291-1294.

Sheng, Y. et al., "Preparation of Spherical Tungsten Powder by RF Induction Plasma", Rare Metal Materials and Engineering, Nov. 2011, vol. 40, No. 11, pp. 2033-2037.

SK makes world's 1st NCM battery with 90% nickel, The Investor, available online <https://www.theinvestor.co.kr/view.php?ud=20200810000820>, dated Aug. 10, 2020, 2 pages.

Suryanarayana, C. et al., "Rapid solidification processing of titanium alloys", International Materials Reviews, 1991, vol. 36, pp. 85-123.

Suryanarayana, C., "Recent Developments in Mechanical Alloying", Reviews on Advanced Materials Science, Aug. 2008, vol. 18(3), pp. 203-211.

Tang, H. P. et al., "Effect of Powder Reuse Times on Additive Manufacturing of Ti—6Al—4V by Selective Electron Beam Melting", JOM, Mar. 2015, vol. 67, pp. 555-563.

Taylor, G., et al.; "Reduction of Metal Oxides by Hydrogen", 1930, vol. 52 (Year: 1930).

Van Laar, J. H. et al., "Spheroidization of Iron Powder in a Microwave Plasma Reactor", Journal of the Southern African Institute of Mining and Metallurgy, Oct. 2016, vol. 116, No. 10, pp. 941-946.

Veith, M. et al., "Low temperature synthesis of nanocrystalline Y3Al5O12 (YAG) and Ce-doped Y3Al5O12 via different sol-gel methods", J. Maler Chem, 1999, pp. 3069-3079.

Walter et al., "Microstructural and mechanical characterization of sol gel-derived Si—O—C glasses" Journal of the European Ceramic Society, vol. 22, Issue 13, Dec. 2002, pp. 2389-2400.

Wang, H., et al., "A detailed kinetic modeling study of aromatics formation in laminar premixed acetylene and ethylene flames" Combustion and Flame, vol. 110, No. 1-2, 1997, pp. 173-221.

Wang, J. et al., "Preparation of Spherical Tungsten and Titanium Powders by RF Induction Plasma Processing", Rare Metals, Jun. 2015 (published online May 31, 2014), vol. 34, No. 6, pp. 431-435.

Wang, Y. et al., "Developments in Nanostructured Cathode Materials for High-Performance Lithium-Ion Batteries", Advanced Materials, Jun. 2008, pp. 2251-2269.

Yang et al., "Preparation of Spherical Titanium Powders from Polygonal Titanium Hydride Powders by Radio Frequency Plasma Treatment" Materials Transactions, vol. 54, No. 12 (2013) pp. 2313-2316.

Zavilopulo, A. N., et al., "Ionization and Dissociative Ionization of Methane Molecules", Technical Physics, vol. 58, No. 9, 2013, pp. 1251-1257.

Zeng, X., et al., "Growth and morphology of carbon nanostructures by microwave-assisted pyrolysis of methane", Physica E., vol. 42, No. 8, 2010, pp. 2103-2108.

Zhang, K., Ph.D., "The Microstructure and Properties of Hipped Powder Ti Alloys", a thesis submitted to The University of Birmingham, College of Engineering and Physical Sciences, Apr. 2009, in 65 pages.

Zhang et al., Microstructures and properties of high-entropy alloys, Progress in Materials Science, vol. 61, 2013, pp. 1-93.

Zhang, H., et al., "Plasma activation of methane for hydrogen production in a N2 rotating gliding arc warm plasma: A chemical kinetics study", Chemical Engineering Journal, vol. 345, 2018, pp. 67-78.

Zhang, J., et al., "Flexible and ion-conducting membrane electrolytes for solid-state lithium batteries: Dispersion of garnet nanoparticles in insulating polyethylene oxide", Nano Energy, vol. 28, 2016, pp. 447-454.

Zhang, X. et al., "High thickness tungsten coating with low oxygen content prepared by air plasma spray", Cailliao Gongcheng. (2014) (5) pp. 23-28 (Year: 2014).

Zhang, Y. D. et al., "High-energy cathode materials for Li-ion batteries: A review of recent developments", Science China Technological Sciences, Sep. 2015, vol. 58(11), pp. 1809-1828.

Zhang, Y. S. et al., "Core-shell structured titanium-nitrogen alloys with high strength, high thermal stability and good plasticity", Scientific Reports, Jan. 2017, vol. 7, in 8 pages.

Zhong, R., et al., "Continuous preparation and formation mechanism of few-layer graphene by gliding arc plasma", Chemical Engineering Journal, vol. 387, 2020, 10 pages.

Zielinski, A et al., "Modeling and Analysis of a Dual-Channel Plasma Torch in Pulsed Mode Operation For Industrial Space, and Launch Applications", IEEE Transactions on Plasma Science, Jul. 2015, vol. 43(7), pp. 2201-2206.

"Build Boldly", Technology Demonstration, 6K Additive, [publication date unknown], in 11 pages.

"High-entropy alloy", Wikipedia, webpage last edited Dec. 29, 2022 (accessed Jan. 17, 2023), in 16 pages. URL: https://en.wikipedia.org/wiki/High-entropy_alloy.

6K, "6K Launches World's First Premium Metal Powders For Additive Manufacturing Derived From Sustainable Sources", Cision PR Newswire, Nov. 4, 2019, in 1 page. URL: https://www.prnewswire.com/news-releases/6k-launches-worlds-first-premium-metal-powders-for-additive-manufacturing-derived-from-sustainable-sources-300950791.html.

Ajayi, B. et al., "A rapid and scalable method for making mixed metal oxide alloys for enabling accelerated materials discovery", Journal of Materials Research, Jun. 2016, vol. 31, No. 11, pp. 1596-1607.

Ajayi, B. P. et al., "Atmospheric plasma spray pyrolysis of lithiated nickel-manganese-cobalt oxides for cathodes in lithium-ion batteries", Chemical Engineering Science, vol. 174, Sep. 14, 2017, pp. 302-310.

Ali, M. et al., Spray Flame Synthesis (SFS) of Lithium Lanthanum Zirconate (LLZO) Solid Electrolyte, Materials, vol. 14, No. 13, 2021, pp. 1-13.

Barbis et al., "Titanium powders from the hydride-dehydride process." Titanium Powder Metallurgy. Butterworth-Heinemann, 2015. pp. 101-116.

Bardos, L., et al., "Differences between microwave and RF activation of nitrogen for the PECVD process", J. Phys. D: Appl. Phys., vol. 15, 1982, pp. 79-82.

Bardos, L., et al., "Microwave Plasma Sources and Methods in Processing Technology", IEEE Press, 2022, 10 pages.

Bobzin, K. et al., "Modelling and Diagnostics of Multiple Cathodes Plasma Torch System for Plasma Spraying", Frontiers of Mechanical Engineering, Sep. 2011, vol. 6, pp. 324-331.

Bobzin, K. et al., "Numerical and Experimental Determination of Plasma Temperature during Air Plasma Spraying with a Multiple Cathodes Torch", Journal of Materials Processing Technology, Oct. 2011, vol. 211, pp. 1620-1628.

Boulos, M. I., "The inductively coupled radio frequency plasma." Journal of High Temperature Material Process, Jan. 1997, vol. 1, pp. 17-39.

Boulos, M., "Induction Plasma Processing of Materials for Powders, Coatings, and Near-Net-Shape Parts", Advanced Materials & Processes, Aug. 2011, pp. 52-53, in 3 pages.

Boulos, M., "Plasma power can make better powders", Metal Powder Report, May 2004, vol. 59(5), pp. 16-21.

Carreon, H. et al., "Study of Aging Effects in a Ti—6AL—4V alloy with Widmanslallen and Equiaxed Microstructures by Nondestructive Means", AIP Conference Proceedings 1581, 2014 (published online Feb. 17, 2015), pp. 739-745.

Chang, S. et al., "One-Step Fast Synthesis of Li4Ti5O12 Particles Using an Atmospheric Pressure Plasma Jet", Journal of the American Ceramic Society, Dec. 26, 2013, vol. 97, No. 3, pp. 708-712.

Chau, J. L. K. et al. "Microwave Plasma Production of Metal Nanopowders," Jun. 12, 2014, Inorganics, vol. 2, pp. 278-290 (Year: 2014).

(56) References Cited

OTHER PUBLICATIONS

Chen, G. et al., "Spherical Ti—6Al—4V Powders Produced by Gas Atomization", Key Engineering Materials, vol. 704, Aug. 2016, pp. 287-292. URL: https://www.scientific.net/KEM.704.287.

Chen, Z., et al., "Advanced cathode materials for lithium-ion batteries", MRS Bulletin, vol. 36, No. 7, 2011, pp. 498-505.

Chikumba et al., "High Entropy Alloys: Development and Applications" 7th International Conference on Latest Trends in Engineering & Technology (ICLTET'2015) Nov. 26-27, 2015 Irene, Pretoria (South Africa).

Choi, S. I., et al., "Continuous process of carbon nanotubes synthesis by decomposition of methane using an arc-jet plasma", Thin Solid Films, 2006, vol. 506-507, 2006, pp. 244-249.

Coldwell, D. M. et al., "The reduction of $SiO_2$ with Carbon in a Plasma", Journal of Electrochemical Society, Jan. 1977, vol. 124, pp. 1686-1689.

Collin, J. E., et al., "Ionization of methane and it's electronic energy levels", Canadian Journal of Chemistry, 2011, vol. 45, No. 16, pp. 1875-1882.

Dearmiti, C., "26. Functional Fillers for Plastics", in Applied Plastics Engineering Handbook—Processing and Materials, ed., Myer Kuiz, Elsevier, 2011, pp. 455-468.

Decker, J., et al., "Sample preparation protocols for realization of reproducible characterization of single-wall carbon nanotubes", Metrologia, 2009, vol. 46, No. 6, pp. 682-692.

Ding, F., et al., "Nucleation and Growth of Single-Walled Carbon Nanotubes: A Molecular Dynamics Study", J. Phys. Chem. B, vol. 108, 2004, pp. 17369-17377.

Ding, F., et al., "The Importance of Strong Carbon-Metal Adhesion for Catalytic Nucleation of Single-Walled Carbon Nanotubes", Nano Letters, 2008, vol. 8, No. 2, pp. 463-468.

Dolbec, R., "Recycling Spherical Powders", Presented at Titanium 2015, Orlando, FL, Oct. 2015, in 20 pages.

Dors, M., et al., "Chemical Kinetics of Methane Pyrolysis in Microwave Plasma at Atmospheric Pressure", Plasma Chem Plasma Process, 2013, vol. 34, No. 2, pp. 313-326.

Eremin, A., et al., "The Role of Methyl Radical in Soot Formation", Combustion Science and Technology, vol. 191, No. 12, 2008, pp. 2226-2242.

Finckle, J. R., et al., "Plasma Pyrolysis of Methane to Hydrogen and Carbon Black", Industrial Engineering and Chemical Research, 2002. Vol. 41, No. 6, 2002, pp. 1425-1435.

Fu, D., et al., "Direct synthesis of Y-junction carbon nanotubes by microwave-assisted pyrolysis of methane", Materials Chemistry and Physics, vol. 118, vol. 2-3, 2009, pp. 501-505.

Fuchs, G.E. et al., "Microstructural evaluation of as-solidified and heat-treated γ-TiAl based powders", Materials Science and Engineering, 1992, A152, pp. 277-282.

Gleiman, S. et al., "Melling and spheroidization of hexagonal boron nitride in a microwave-powered, atmospheric pressure nitrogen plasma", Journal of Materials Science, Aug. 2002, vol. 37(16), pp. 3429-3440.

Grace, J. et al., "Connecting particle sphericity and circularity", Particuology, vol. 54, 2021, pp. 1-4, ISSN 1674-2001, https://doi.org/10.1016/j.partic.2020.09.006. (Year: 2020).

Gradl, P. et al., "GRCop-42 Development and Hot-fire Testing Using Additive Manufacturing Powder Bed Fusion for Channel-Cooled Combustion Chambers", 55th AIAA/SAE/ASEE Joint Propulsion Conference 2019, Aug. 2019, pp. 1-26.

Haghighatpanah, S., et al., "Computational studies of catalyst-free single walled carbon nanotube growth", J Chem Phys, vol. 139, No. 5, 10 pages.

Haneklaus, N., et al., "Stop Smoking—Tube-In-Tube Helical System for Flameless Calcination of Minerals", Processes, vol. 5, No. 4, 2017, pp. 1-12.

He et al., "A precipitation-hardened high-entropy alloy with outstanding tensile properties" Acta Materialia 102, Jan. 2016, pp. 187-196.

Houmes et al., "Microwave Synthesis of Ternary Nitride Materials", Journal of Solid State Chemistry, vol. 130, Issue 2, May 1997, pp. 266-271.

Huo, H., et al., "Composite electrolytes of polyethylene oxides/garnets interfacially wetted by ionic liquid for room-temperature solid-state lithium battery", Journal of Power Sources, vol. 372, 2017, pp. 1-7.

Irle, S., et al., "Milestones in molecular dynamics simulations of single-walled carbon nanotube formation: A brief critical review", Nano Research, 2009, vol. 2, No. 10, 14 pages.

Ivasishin, et al., "Innovative Process for Manufacturing Hydrogenated Titanium Powder for Solid State Production of R/M Titanium Alloy Components" Titanium 2010, Oct. 3-6, 2010, 27 pages.

Jasek, O., et al., "Microwave plasma-based high temperature dehydrogenation of hydrocarbons and alcohols as a single route to highly efficient gas phase synthesis of freestanding graphene", Nanotechnology, 2021, vol. 32, 11 pages.

Jasinski, M., et al., "Atmospheric pressure microwave plasma source for hydrogen production", International Journal of Hydrogen Energy, vol. 38, Issue 26, 2013, pp. 11473-11483.

Jasinski, M., et al., "Hydrogen production via methane reforming using various microwave plasma sources", Chem. Listy, 2008, vol. 102, pp. s1332-s1337.

Jia, H. et al., "Hierarchical porous silicon structures with extraordinary mechanical strength as high-performance lithium-ion battery anodes", Nature Communications, Mar. 2020, vol. 11, in 9 pages. URL: https://doi.ora/10.1038/s41467-020-15217-9.

Kassel, L. S., "The Thermal Decomposition of Methane", Journal of the American Chemical Society, vol. 54, No. 10, 1932, pp. 3949-3961.

Kerscher, F., et al., "Low-carbon hydrogen production via electron beam plasma methane pyrolysis: Techno-economic analysis and carbon footprint assessment", International Journal of Hydrogen Energy, vol. 46, Issue 38, 2021, pp. 19897-19912.

Kim, H., et al., "Three-Dimensional Porous Silicon Particles for Use in High-Performance Lithium Secondary Batteries", Angewandte Chemie International Edition, vol. 47, No. 2, Dec. 15, 2008, pp. 10151-10154.

\* cited by examiner

SYSTEMS, METHODS, AND DEVICE FOR PYROLYSIS OF METHANE IN A MICROWAVE PLASMA FOR HYDROGEN AND STRUCTURED CARBON POWDER PRODUCTION

INCORPORATION BY REFERENCE TO ANY PRIORITY APPLICATIONS

This application claims the priority benefit under 35 U.S.C. § 119(e) of U.S. Provisional Application No. 63/387,669, filed Dec. 15, 2022, the entire disclosure of which is incorporated herein by reference in its entirety. Any and all applications for which a foreign or domestic priority claim is identified in the Application Data Sheet as filed with the present application are hereby incorporated by reference under 37 CFR 1.57.

BACKGROUND

Field

The present disclosure is generally directed to structured carbon and hydrogen and methods of production thereof.

Description

Using methane in a plasma torch is established as a possible method for various industrial processes including hydrogen generation, acetylene formation, and many other hydrocarbon formations and carbon nanotube (CNT) formation has been shown to occur during the pyrolysis of methane under certain conditions. This would be hugely beneficial as the CNTs produced via this method would not require additional purification steps which often reduce the quality.

Microwave plasma technology has provided stable hydrogen-based plasma for many years. Additional hot zone technologies are uniquely positioned at this time to attempt the controlled pyrolysis of methane to produce bulk hydrogen and CNTs. Novel methods for producing carbon structures and hydrogen are presented herein.

SUMMARY

For purposes of this summary, certain aspects, advantages, and novel features of the invention are described herein. It is to be understood that not all such advantages necessarily may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

Some embodiments herein are directed to methods for producing a structured carbon powder using a microwave generated plasma, the method comprising: injecting a plasma gas comprising methane ($CH_4$) into a liner, the liner in communication with a microwave waveguide; propagating microwaves through the microwave waveguide, the microwaves generated using a microwave generator; and generating a microwave plasma by contacting the plasma gas with the microwaves, wherein contacting the plasma gas with the microwaves pyrolyzes the plasma gas into pyrolysis products, wherein the pyrolysis products comprise hydrogen gas and solid carbon, and wherein the solid carbon comprises a sheet or platelet microstructure.

In some embodiments, a pressure within the liner and the reaction chamber is 760 Torr. In some embodiments, a frequency of the microwaves is between about 300 MHz and about 300 GHz. In some embodiments, a frequency of the microwaves is about 915 MHz.

In some embodiments, the exhausting the ionized plasma gas from the liner into the reaction chamber comprises directing the ionized plasma gas through an extension tube at an exit of the liner. In some embodiments, the extension tube comprises graphite. In some embodiments, the liner comprises quartz.

In some embodiments, the plasma gas comprises between about 0 vol % and about 5 vol %. In some embodiments, the solid carbon comprises a sheet microstructure, and wherein edges of the carbon sheets measure between about 100 nm and about 1000 nm. In some embodiments, the solid carbon comprises a sheet microstructure, and wherein edges of the carbon sheets measure between about 50 nm and about 150 nm.

In some embodiments, the solid carbon comprises substantially no amorphous carbon. In some embodiments, the solid carbon comprises substantially no carbon nanotubes. In some embodiments, the solid carbon comprises nanosheets of graphene.

In some embodiments, the pyrolysis products comprise acetylene ($C_2H_2$). In some embodiments, the pyrolysis products comprise at least one of $CH_3$, $C_2H_5$, and $C_2H_3$.

In some embodiments, the plasma gas is contacted with the microwaves in the absence of a catalyst. In some embodiments, the plasma gas comprises argon (Ar). In some embodiments, the plasma gas comprises hydrogen ($H_2$). In some embodiments, the plasma gas is injected into the liner at a temperature above 500° C. In some embodiments, the solid carbon is solidified in the gas phase.

BRIEF DESCRIPTION OF THE DRAWINGS

The drawings are provided to illustrate example embodiments and are not intended to limit the scope of the disclosure. A better understanding of the systems and methods described herein will be appreciated upon reference to the following description in conjunction with the accompanying drawings, wherein.

DETAILED DESCRIPTION

Figure 1:
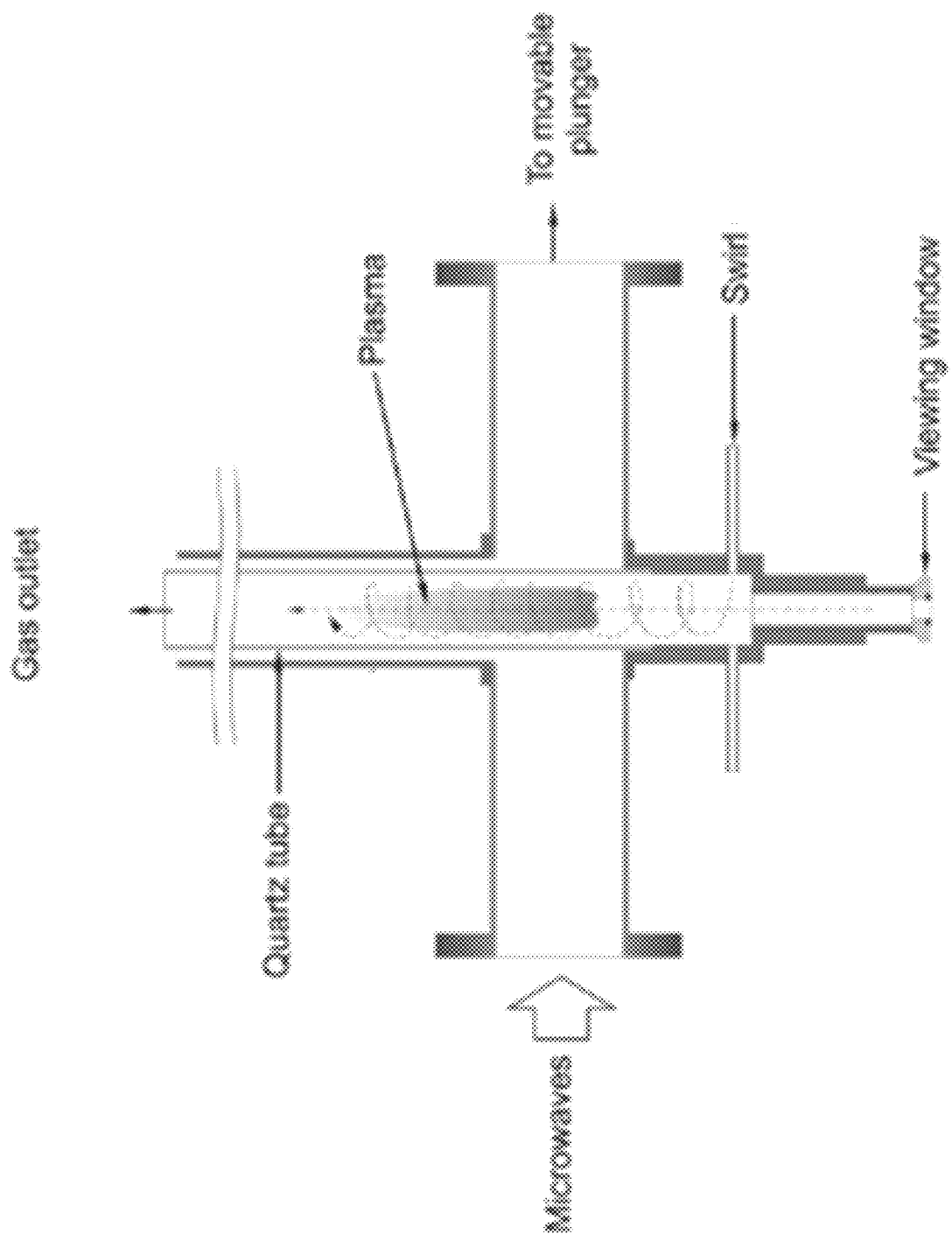
FIG. 1 illustrates a diagram of an example swirl flow microwave plasma system according to some embodiments herein.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the invention is defined solely by the claims. The features illustrated or described in connection with one exemplary embodiment may be combined with the features of other embodiments. Such modifications and variations are intended to be included within the scope of the present technology.

In some embodiments, microwave plasma processes to perform pyrolysis of methane gas composition and carbon morphology are provided herein. The microwave plasma technologies described herein provide energy efficiency compared to traditional methods of material synthesis and purification, precise control over material composition. Furthermore, materials produced using the microwave plasma technology described herein may high purity levels, making them suitable for applications where material quality is critical. Furthermore, microwave plasma processes are environmentally sustainable compared to traditional processing methods due to reduced energy consumption and waste generation.

In some embodiments, the microwave plasma processes described herein may be used to produce high-quality carbon structures, such as carbon nanotubes (CNTs). Although CNTs) may be formed during carbon formation, in some embodiments, a high percentage of carbon may be converted to graphene nanoplatelets. In some embodiments, the composition of the gas products may be consistent with partial pyrolysis of methane with a high degree of acetylene production as well as hydrogen gas.

Some embodiments herein relate to the use of microwave plasma processing to produce carbon structures and bulk hydrogen. A microwave plasma at atmospheric pressure is generally considered a thermal plasma, i.e., electrons and ions have energy at the same level due to high collision frequency. However, the degree of ionization may not be exceedingly high, only about 10% of gas particles becoming ionized. While the ion energies in microwave plasmas are lower than those of higher potential direct-current (DC) arc systems, the electron energies are quite high. This makes microwave plasma good for forming radicals which can be used to enhance or even initiate certain chemical steps which would otherwise not occur at these pressures and temperatures. The chemical species present in radio frequency (RF) plasma at higher powers compared to that of lower power in microwave plasma show that a higher intensity and degree of radicals are present in the microwave plasma relative to the RF.

Plasma torches generate and provide high temperature directed flows of plasma for a variety of purposes. The two main types of plasma torches are induction plasma torches and microwave plasma torches. Generally, inductive plasmas suffer from plasma non-uniformity. This non-uniformity leads to limitations on the ability of inductive plasmas to process certain materials. Furthermore, significant differences exist between the microwave plasma apparatuses and other plasma generation torches, such as induction plasma. For example, microwave plasma is hotter on the interior of the plasma plume, while induction is hotter on the outside of the plumes. In particular, the outer region of an induction plasma can reach about 10,000 K while the inside processing region may only reach about 1,000 K. This large temperature difference leads to material processing and feeding problems. Furthermore, induction plasma apparatuses are unable to process feedstocks at low enough temperatures to avoid melting of certain feed materials without extinguishing the plasma.

Unlike other plasma systems driven by high voltage potentials (e.g., DC arc), in some embodiments, microwave plasmas are primarily driven by the avalanche effect with an initial seed of free electrons required to begin the plasma. In some embodiments, joule heating of the gas follows as the ionized gases couple the microwave energy like an antenna and continue to heat the surrounding gases. An example microwave plasma torch setup according to some embodiment is shown in FIG. 1. In some embodiments, the plasma gas is injected into a quartz liner which runs through a microwave waveguide where microwaves are applied to the plasma gas. The ionized gas is then exhausted into a chamber where mixing and recombination of the ionized species may occur.

In some embodiments, two main methods of methane breakdown may occur: ionization and pyrolysis. Ionization of gas is the act of coupling enough energy into the gas molecule to raise an electron out of the gas molecule's orbital level. In the case of methane, there are many ionization states which can occur. For example, an electron may be stripped, creating $CH_4+$. Then, in some embodiments, for example, a hydrogen atom may be stripped, creating $CH_3+$, and so on until $C+$. The ionization energy required to reduce methane starts at 12.62 eV for $CH_4+$ and increases to 25 eV for $C+$. The lowest energy level is $CH_4+$ at 12.62 cV due to the loosely bound 112 orbital electron. In some embodiments, there may be an instability due to the Jahn-Teller effect which results in multiple products from this ionization and the eV required is between 12.51 and 12.71 eV. However, in some embodiments, since the energy level of a microwave field at, e.g., 915 MHz, is well below that level, the primary method of decomposition of methane will be through pyrolysis and not direct ionization. The energy level may be calculated according to the below equation, wherein eV is the energy in the electromagnetic filed, h is Plank's constant, c is the speed of light, and A is the wavelength of the electromagnetic waves.

$$eV = \frac{hc}{\lambda}$$

Figure 2:
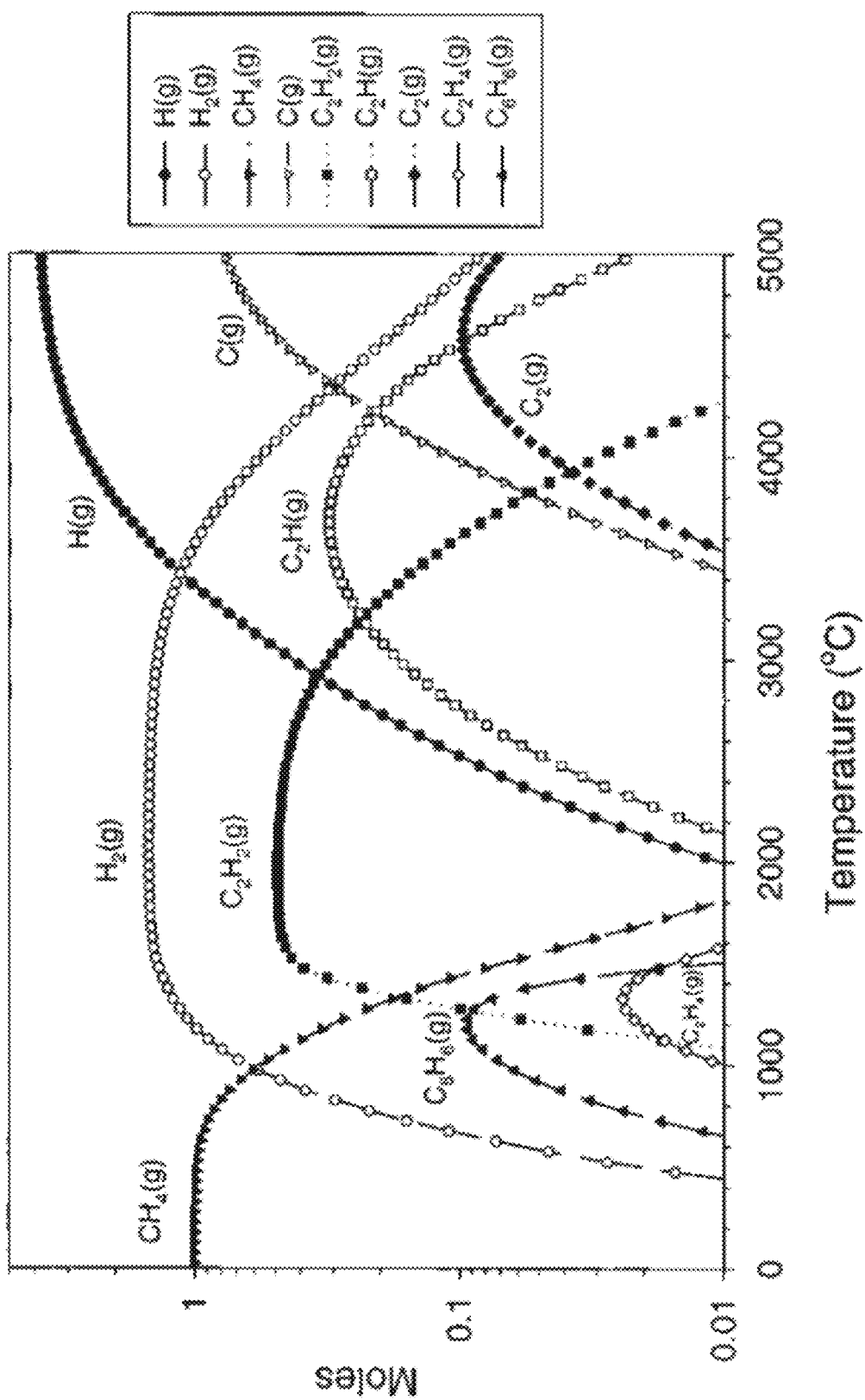
FIG. 2 illustrates a simplified equilibrium diagram for 1 mol of methane with solid carbon omitted according to some embodiments herein.

Pyrolysis of methane by simple thermal breakdown begins at 500° C. and finishes around 1000° C., and at thermodynamic equilibrium produces the by-products solid carbon and molecular hydrogen gas. The standard model referenced when discussing methane pyrolysis is by the unimolecular dissociation of hydrogen molecules from methane to gradually lower hydrogenated carbon radicals. However, this study was performed over long time periods and at temperatures much lower than those present in a microwave thermal plasma, such as that used in some embodiments herein. With short residence times, omitting solid carbon from the equilibrium diagram is more appropriate to understand the immediate concentrations leaving the plasma and is shown in FIG. 2. In some embodiments, the primary by-product besides hydrogen gas may comprise acetylene ($C_2H_2$) which is stable to high temperatures.

Figure 3:
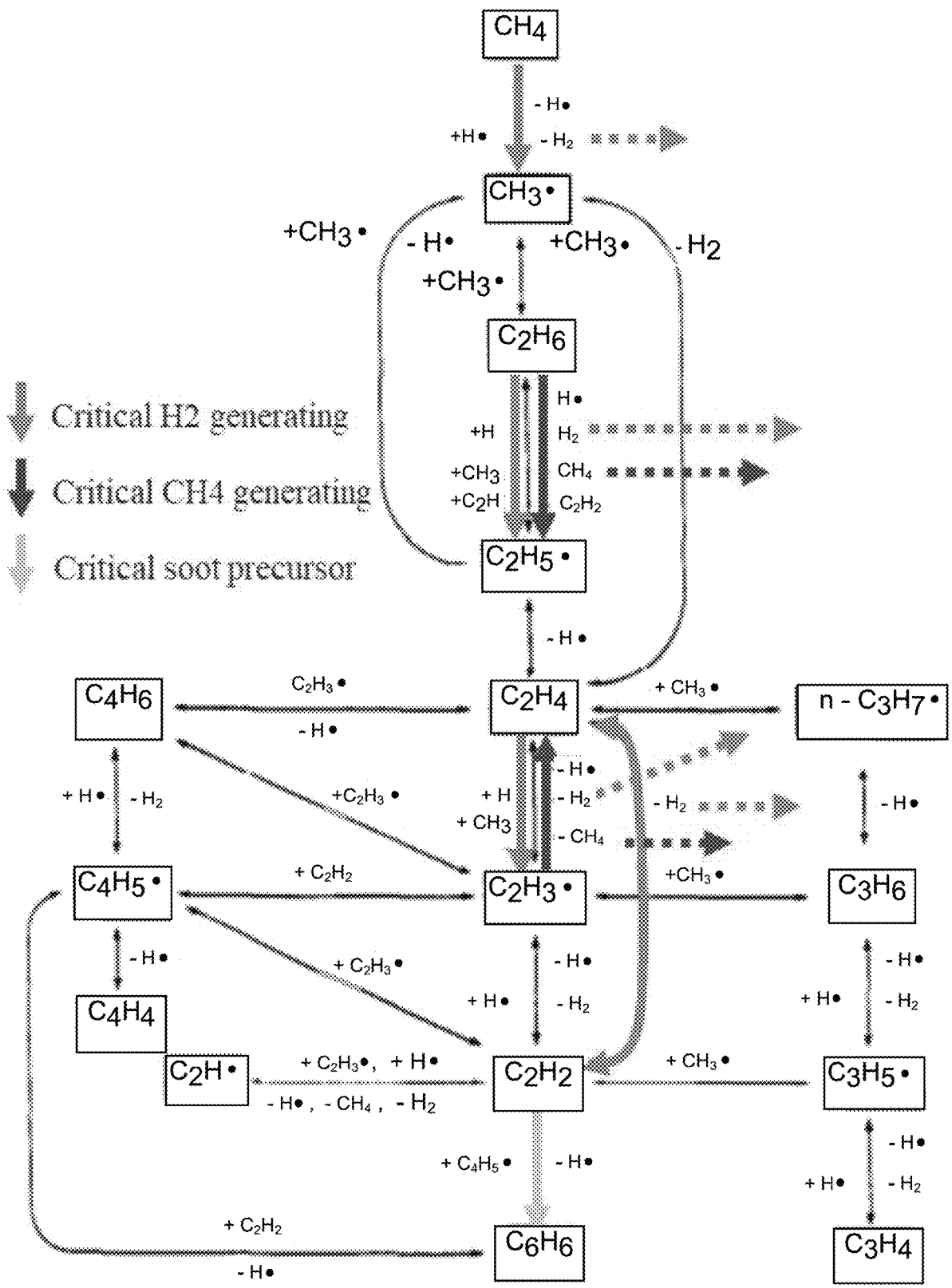
FIG. 3 illustrates an example diagram of the total methane decomposition reaction tree according to some embodiments herein.

Table 1 lists the critical reactions for hydrogen generation via methane pyrolysis when considering a temperature between about 1500 K and about 2000 K over a time of about 37 ms. Modelling the pyrolysis of methane has shown that the primary source of hydrogen gas is R1 with secondary reactions with ethylene (R2) and ethane (R3, R4) decomposition accounting for about 10% or less. In some embodiments, R1 and R5 are the most important for methane conversion with over 99% of methane decomposing via these mechanisms. In some embodiments, methane decomposition is not the only process that can occur but also methane recombination. In some embodiments, reactions R6 and R7 are the primary mechanisms via which methane is shown to be generated in the complicated soup of hydrocarbons that can be present during methane decomposition. FIG. 3 illustrates an example diagram of the total methane decomposition reaction tree according to some embodiments herein.

In some embodiments, during the pyrolysis of methane, the two equilibrium products are hydrogen gas and solid carbon. In some embodiments, the form of the solid carbon is dependent on many factors. Typically, in some embodiments, if the solid carbon is quenched on a surface, coal coke is formed. In some embodiments, if the carbon is solidified in the gas phase, the formation of carbon black may occur. The most recognized method for carbon black formation is by polycyclic aromatic hydrocarbons (PAH) acting as nucleation points for soot growth. Benzene or phenyl rings lose a hydrogen atom to the monoatomic hydrogen in the gas stream and an acetylene molecule bonds to the radical site which results in surface growth of soot particles. This mechanism is referred to as the Hydrogen Abstraction Acetylene Addition (HACA). Heterogeneous nucleation of solid carbon in an acetylene flame is known to occur on PAHs, the precursor to which is benzene ($C_6H_6$). Solid carbon growth in this environment is assumed to progress by the adsorption of acetylene on the surface and the abstraction of hydrogen. Modelling using this assumption has shown that solid carbon growth stops once the temperature is below about 1500 K. Therefore, the presence for both benzine and acetylene may be important factors in the nucleation and growth rate of solid carbon particles. Another allotrope of carbon is CNTs whose nucleation and growth mechanisms have been studied extensively and is still debated. In the vapor-liquid-solid (VLS) model, carbon atoms are adsorbed to catalyst particles, typically a transition metal such as Ni, Fe, or Co, until supersaturated. At this point the carbon atoms may form a graphene like lattice, often called the "cap." The cap may be pushed up and away from the catalyst particle as carbon atoms diffuse into the sp2 carbon lattice which may form. The importance of the catalyst particles is thought to have four points: preventing the closure of the carbon nanotube lattice, functionalizing the edges of the nanotube, converting the feedstock (hydrocarbon, CO, etc.) into carbon atoms, and serving as a driving force for sp2 lattice formation by supersaturating with carbon atoms.

However, in some embodiments, carbon nanotubes can be formed without a catalyst. The mechanism behind this growth is still under investigation but oxides appear to be the primary substrate. Additionally, carbon nanotubes may be created without any catalyst by heating methane through a carbon felt in a microwave chamber. Without being limited by theory, the rapid heating and the microwave environment assisted in exciting free radical species from the methane which could become nucleation points for nanotube growth. Some embodiments herein are directed to using, for example, atmospheric microwave plasma system to dissociate methane and create carbon microstructures in the

TABLE 1

List of critical chemical reactions for methane pyrolysis.

| No. | Reaction | A (mol + cm⁻3 + s¹) | n | E (kcal/mol) | Critical |
|---|---|---|---|---|---|
| R1 | $CH_4 + H \leftrightarrow CH_3 + H_2$ | 2.19e−20 | 3 | 8.037 | H, M |
| R2 | $C_2H_6 + H \leftrightarrow C_2H_5 + H_2$ | 2.41e−15 | 0 | 7.411 | H |
| R3 | $C_2H_4 + M \leftrightarrow C_2H_2 + H_2 + M$ | 1.65e−07 | 0 | 71.54 | H, A |
| R4 | $C_2H_4 + H \leftrightarrow C_2H_3 + H_2$ | 9.0e−10 | 0 | 14.9 | H |
| R5 | $H + CH_3 + M \leftrightarrow CH_4 + M$ | 3.88e−24 | −1.8 | 0 | M |
| R6 | $C_2H_6 + CH_3 \leftrightarrow C_2H_5 + CH_4$ | 2.51e−31 | 6 | 6.046 | M+ |
| R7 | $C_2H_4 + CH_3 \leftrightarrow CH_4 + C_2H_3$ | 6.91e−12 | 0 | 11.128 | M+ |
| R8 | $C_2H_2 + H + M \leftrightarrow C_2H_3 + M$ | 9.45e−30 | 0 | 1.47 | A |

Legend: H = hydrogen generation, M = methane conversion, A = acetylene formation, M+ = methane recombination. Arrhenius rate equation constants $k(T) = AT^n e^{E/RT}$ resulting soot without using catalyst particles. In some embodiments, a graphite extension tube may be used to supply additional carbon radicals during methane decomposition.

Microwave Plasma Apparatus

In some embodiments, a microwave plasma apparatus may be used in the production of carbon structures according to the embodiments herein. In some embodiments, the microwave plasma apparatus may comprise a microwave generator for generating microwaves at a frequency between 300 MHz and 300 GHz, such as, for example, 915 Mhz.

In some embodiments, the microwave plasma apparatus may comprise a gas mixing panel, plasma torch with quartz liner, water-cooled stainless-steel reactor, water cooled exhaust and water separation particle filter. In some embodiments monitoring instrumentation may be provided, including a machine vision camera, one or more thermocouples, one or more inspection ports, such as at the liner exit, and mass spectrometer, such as in the exhaust after the water-cooled sections.

In some embodiments, a graphite extension tube may be provided. In some embodiments, the extension tube extends downward into a reaction chamber of the microwave plasma apparatus, the extension tube confining and directing the microwave plasma to extend its length. In some embodiments, the extension tube may concentrate the energy and power provided by a microwave power source, in order to form a longer microwave plasma within the apparatus. The methods and apparatuses described herein may utilize an extension tube, which extends downward from a core plasma tube into the reaction chamber. In some embodiments, the extension tube may concentrate energy from the microwave power source into a smaller volume, extending and directing the plasma at a greater length than would be possible using a conventional microwave plasma apparatus. In some embodiments, a length of a plasma may be tuned or altered by configuring one or more of the following parameters: power, plasma gas flow, type of gas, extension tube material, level of insulation of the reactor chamber or the extension tube, level of coating of extension tube, and geometry of the extension tube (e.g., tapered/stepped).

Furthermore, in some embodiments, an agitator, vibrator, or other device may be provided to prevent sticking and/or to remove feedstock particles from surfaces of the extension tube. In some embodiments, providing an extension tube with a specific shape may facilitate prevention of material accumulation on one or more surfaces of the microwave plasma torch. For example, a conical extension tube may prevent buildup on surfaces of the extension tube.

In some embodiments, an extension tube as described herein may extend downward into the reaction chamber of a microwave plasma apparatus. In some embodiments, the extension tube may extend downward at a length of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the reaction chamber length, or any value between the aforementioned values.

Various parameters of the microwave plasma may be adjusted manually or automatically in order to achieve a desired material. These parameters may include, for example, power, plasma gas flow rates, type of plasma gas, presence of an extension tube, extension tube material, level of insulation of the reactor chamber or the extension tube, level of coating of the extension tube, geometry of the extension tube (e.g. tapered/stepped), feed material size, feed material insertion rate, feed material inlet location, feed material inlet orientation, number of feed material inlets, plasma temperature, residence time and cooling rates. The resulting material may exit the plasma into a sealed chamber where the material is quenched then collected. In some embodiments, the extension tube may comprise isomolded graphite and be held up by, for example, a stainless sheet scaffold. In some embodiments, the top edge of the extension tube may be machined to fit over the quartz liner to create a seamless extension of the plasma containment.

In some embodiments, the microwave plasma apparatus may be operated at atmospheric pressure (760 Torr). In some embodiments, before running, the chamber may be purged to below 100 ppm oxygen using argon gas before striking plasma. In some embodiments, after processing and once the chamber temperature has fallen below 50° C., compressed dry air (CDA) may be slowly added in 5 vol % increments with Argon until 100 vol % CDA fills the chamber.

Figure 4:
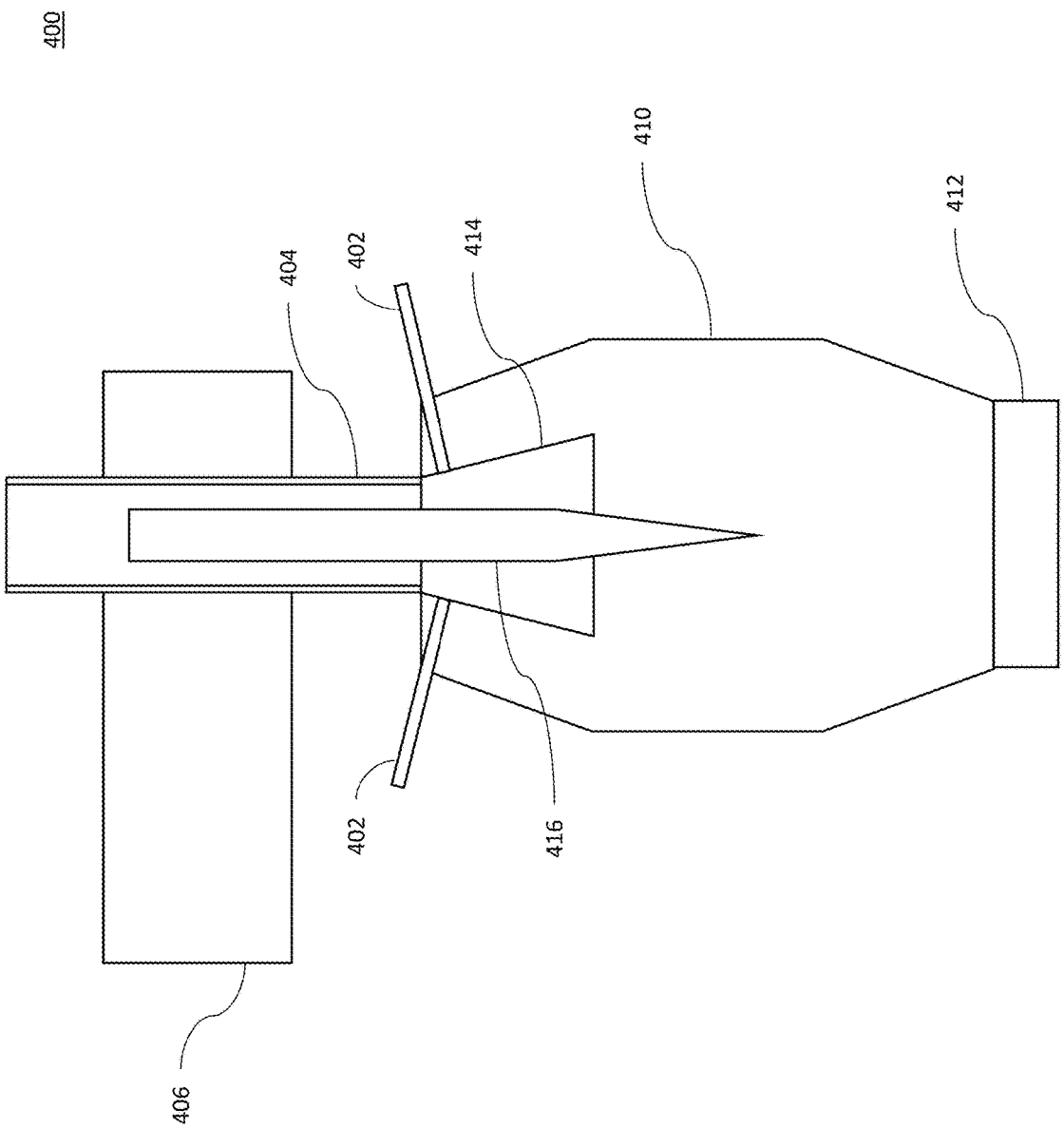
FIG. 4 illustrates an embodiment of a microwave plasma torch that can be used in the production of materials according to some embodiments herein.

FIG. 4 illustrates an embodiment of a microwave plasma torch 400 that can be used in the production of materials according to some embodiments herein. In some embodiments, a feedstock can be introduced, via one or more feedstock inlets 402, into a microwave plasma 416. In some embodiments, an entrainment gas flow and/or a sheath flow may be injected into the microwave plasma torch 400 to create flow conditions within the plasma torch prior to ignition of the plasma 416 via microwave radiation source 406. In some embodiments, the entrainment flow and sheath flow are both axis-symmetric and laminar, while in other embodiments the gas flows are swirling. In some embodiments, the feedstock may be introduced into the microwave plasma torch 400, where the feedstock may be entrained by a gas flow that directs the materials toward the plasma 416.

The gas flows can comprise a noble gas column of the periodic table, such as helium, neon, argon, etc. Although the gases described above may be used, it is to be understood that a variety of gases can be used depending on the desired material and processing conditions. In some embodiments, within the microwave plasma 416, the feedstock may undergo a physical and/or chemical transformation. Inlets 402 can be used to introduce process gases to entrain and accelerate the feedstock towards plasma 416. In some embodiments, a second gas flow can be created to provide sheathing for the inside wall of a core gas tube or liner 404 and a reaction chamber 410 to protect those structures from melting due to heat radiation from plasma 416.

Various parameters of the microwave plasma 416 may be adjusted manually or automatically in order to achieve a desired material. These parameters may include, for example, power, plasma gas flow rates, type of plasma gas, presence of an extension tube, extension tube material, level of insulation of the reactor chamber or the extension tube, level of coating of the extension tube, geometry of the extension tube (e.g. tapered/stepped), feed material size, feed material insertion rate, feed material inlet location, feed material inlet orientation, number of feed material inlets, plasma temperature, residence time and cooling rates. The resulting material may exit the plasma into a sealed chamber 412 where the material is quenched then collected.

In some embodiments, the feedstock is injected after the microwave plasma torch applicator for processing in the "plume" or "exhaust" of the microwave plasma torch. Thus, the plasma of the microwave plasma torch is engaged at the exit end of the plasma torch core tube 404, or further downstream. In some embodiments, adjustable downstream feeding allows engaging the feedstock with the plasma plume downstream at a temperature suitable for optimal melting of feedstock through precise targeting of temperature level and residence time. Adjusting the inlet location and plasma characteristics may allow for further customization of material characteristics. Furthermore, in some embodiments, by adjusting power, gas flow rates, pressure, and equipment configuration (e.g., introducing an extension tube), the length of the plasma plume may be adjusted.

In some embodiments, feeding configurations may include one or more individual feeding nozzles surrounding the plasma plume. The feedstock may enter the plasma from any direction and can be fed in 360° around the plasma depending on the placement and orientation of the inlets 402. Furthermore, the feedstock may enter the plasma at a specific position along the length of the plasma 416 by adjusting placement of the inlets 402, where a specific temperature has been measured and a residence time estimated for providing the desirable characteristics of the resulting material.

In some embodiments, the angle of the inlets 402 relative to the plasma 416 may be adjusted, such that the feedstock can be injected at any angle relative to the plasma 416. For example, the inlets 102 may be adjusted, such that the feedstock may be injected into the plasma at an angle of about 0 degrees, about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, or about 90 degrees relative to the direction of the plasma 416, or between any of the aforementioned values.

In some embodiments, implementation of the downstream injection method may use a downstream swirl or quenching. A downstream swirl refers to an additional swirl component that can be introduced downstream from the plasma torch to keep the powder from the walls of the core tube 404, the reactor chamber 410, and/or an extension tube 414.

In some embodiments, the extension tube may extend into the reaction chamber of a microwave plasma apparatus. In some embodiments, the extension tube may comprise a stepped shape, such that the tube comprises one or more cylindrical volumes extending downward in the reaction chamber, wherein each successive cylindrical volume comprises a larger diameter than each previous cylindrical volume as the tube extends downward in the reaction chamber. In some embodiments, the extension tube may have a conical shape, tapering radially outwards as it extends downward into the reaction chamber. In some embodiments, the extension tube may comprise a single cylindrical volume.

In some embodiments, the extension tube may have a dual conical shape, where the first conical shape tapers radially outwards as it extends downward into the reaction chamber, and the second conical shape is an inverted asymmetrical shape to the first conical shape and is connected to the end of the first conical shape and tapers radially inwards as it extends downward into the reaction chamber. In some embodiments, the extension tube may comprise a dual conical shape, where the widest portion of the first conical shape is connected to the widest portion of the second conical shape. In some embodiments, the length of the first conical shape is greater than the length of the second conical shape.

In some embodiments, the extension tube may have a dual conical shape, where the first conical shape tapers radially outwards as it extends downward into the reaction chamber and the second conical shape is an inverted symmetrical shape to the first conical shape and is connected to the end of the first conical shape and tapers radially inwards as it extends downward into the reaction chamber. In some embodiments, the widest portion of the first conical shape is connected to the widest portion of the second conical shape. In some embodiments, the length of the first conical shape is equal to the length of the second conical shape. In some embodiments, the length of the second conical shape is greater than the length of the first conical shape. In some embodiments, the feed material inlets may insert feedstock within the extension tube.

In some embodiments, the extension tube may comprise a length of about 1 foot. In some embodiments, the extension tube may comprise a length of about 1 inch, about 2 inches, about 3 inches, about 4 inches, about 5 inches, about 6 inches, about 7 inches, about 8 inches, about 9 inches, about 10 inches, about 11 inches, about 1 foot, about 2 feet, about 3 feet, about 4 feet, about 5 feet, about 6 feet, about 7 feet, about 8 feet, about 9 feet, about 10 feet, about 11 feet, about 12 feet, about 13 feet, about 14 feet, about 15 feet, about 16 feet, about 17 feet, about 18 feet, about 19 feet, about 20 feet, about 21 feet, about 22 feet, about 23 feet, about 24 feet, about 25 feet, about 26 feet, about 27 feet, about 28 feet, about 29 feet, or about 30 feet, or any value between the aforementioned values.

In some embodiments, the length of a reaction chamber 410 of a microwave plasma apparatus may be about 1 foot, about 2 feet, about 3 feet, about 4 feet, about 5 feet, about 6 feet, about 7 feet, about 8 feet, about 9 feet, about 10 feet, about 11 feet, about 12 feet, about 13 feet, about 14 feet, about 15 feet, about 16 feet, about 17 feet, about 18 feet, about 19 feet, about 20 feet, about 21 feet, about 22 feet, about 23 feet, about 24 feet, about 25 feet, about 26 feet, about 27 feet, about 28 feet, about 29 feet, or about 30 feet, or any value between the aforementioned values.

In some embodiments, the length of the plasma 416, which may be extended by adjusting various processing conditions and equipment configurations, may be about 1 foot, about 2 feet, about 3 feet, about 4 feet, about 5 feet, about 6 feet, about 7 feet, about 8 feet, about 9 feet, about 10 feet, about 11 feet, about 12 feet, about 13 feet, about 14 feet, about 15 feet, about 16 feet, about 17 feet, about 18 feet, about 19 feet, about 20 feet, about 21 feet, about 22 feet, about 23 feet, about 24 feet, about 25 feet, about 26 feet, about 27 feet, about 28 feet, about 29 feet, or about 30 feet, or any value between the aforementioned values.

In some embodiments, the entrainment flow and sheath flow are both axis-symmetric and laminar, while in other embodiments the gas flows are swirling. The feed materials may be introduced axially into the microwave plasma torch, where they are entrained by a gas flow that directs the materials toward the plasma. Within the microwave generated plasma, the feed materials may be melted or partially melted in order to spheroidize the materials. Inlets can be used to introduce process gases to entrain and accelerate particles towards the plasma. In some embodiments, particles are accelerated by entrainment using a core laminar gas flow created through an annular gap within the plasma torch. A second laminar flow can be created through a second annular gap to provide laminar sheathing for the inside wall of dielectric torch to protect the wall from melting due to heat radiation from plasma. In some embodiments, the laminar flows direct particles toward the plasma along a path as close as possible to a central axis of the plasma, exposing the particles to a substantially uniform temperature within the plasma.

In some embodiments, suitable flow conditions are present to keep particles from reaching the inner wall of the plasma torch where plasma attachment could take place. In some embodiments, particles are guided by the gas flows towards the microwave plasma, where each particle undergoes homogeneous thermal treatment. Various parameters of the microwave generated plasma, as well as particle parameters, may be adjusted in order to achieve desired results. These parameters may include microwave power, feed material size, feed material insertion rate, gas flow rates, plasma temperature, residence time and cooling rates. In some embodiments, the cooling or quenching rate is not less than $10^{+3}$ degrees C./sec upon exiting the plasma. As discussed above, in some embodiments, the gas flows are laminar; however, in alternative embodiments, swirl flows or turbulent flows may be used to direct the feed materials toward the plasma.

Figure 5A:
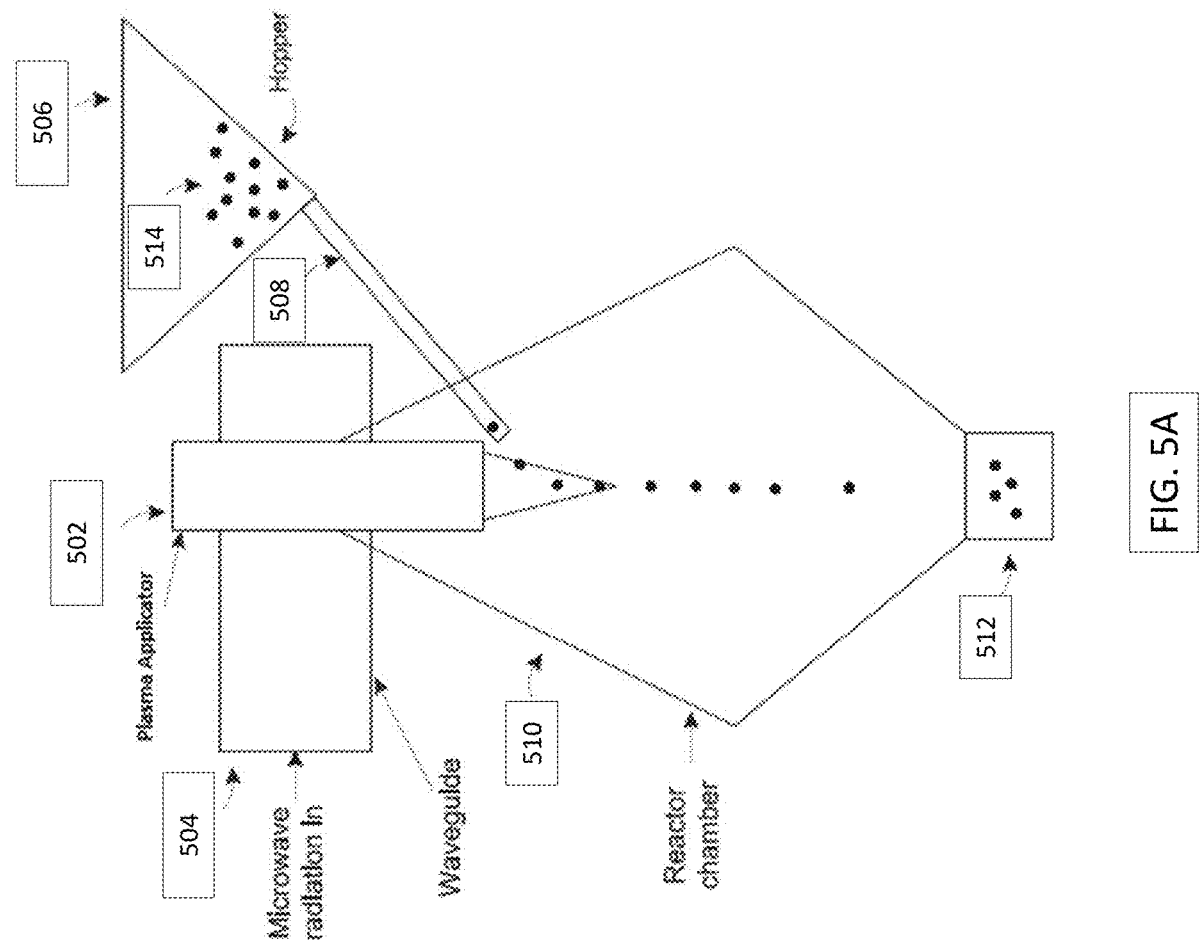
FIGS. 5A-B illustrate an exemplary microwave plasma torch that includes a side feeding hopper, thus allowing for downstream feeding, according to some embodiments herein.
Figure 5B:
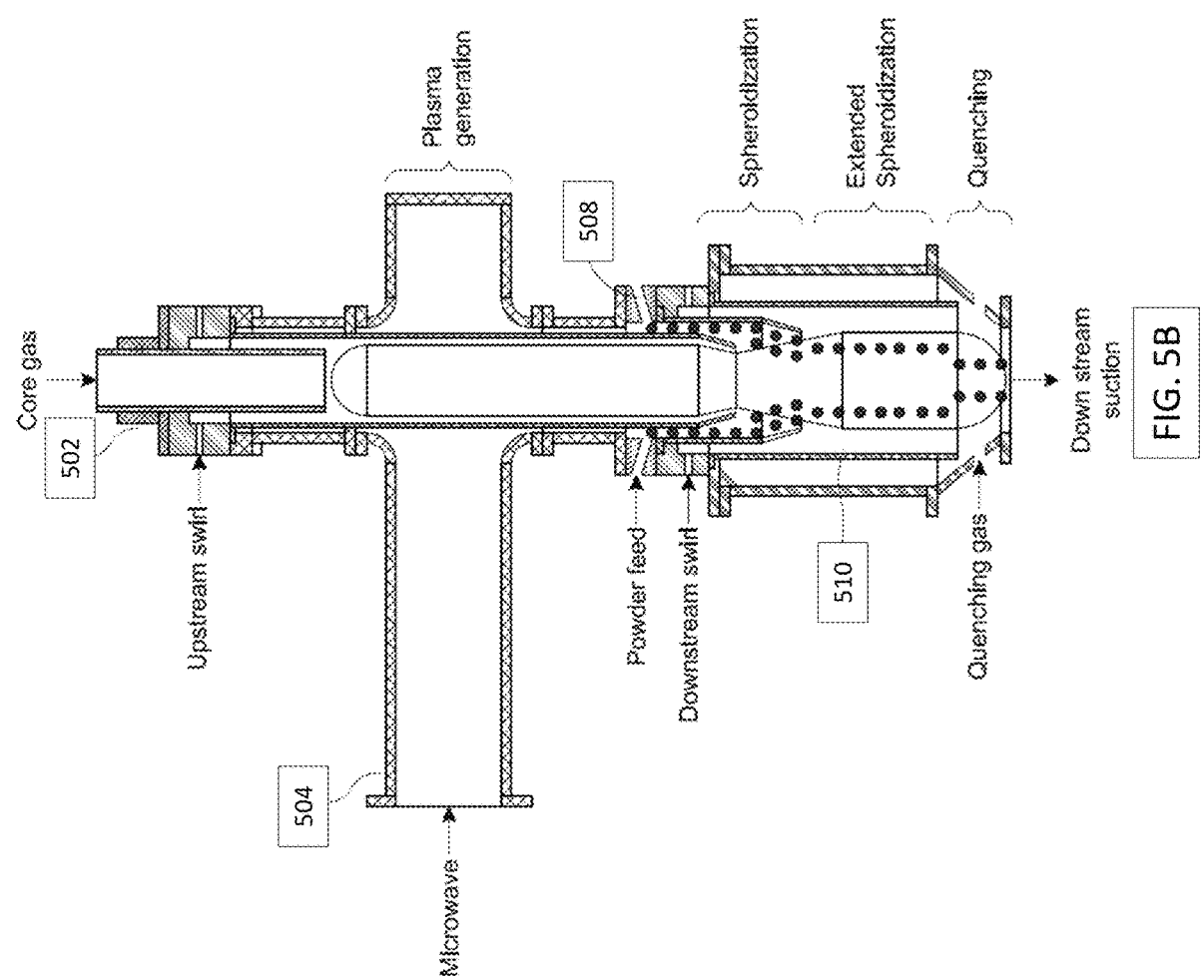

FIGS. 5A-B illustrate an exemplary microwave plasma torch that includes a side feeding hopper, thus allowing for downstream feeding. Thus, in this implementation the feedstock is injected after the microwave plasma torch applicator for processing in the "plume" or "exhaust" of the microwave plasma torch. Thus, the plasma of the microwave plasma torch is engaged at the exit end of the plasma torch to allow downstream feeding of the feedstock. This downstream feeding can advantageously extend the lifetime of the torch as the hot zone is preserved indefinitely from any material deposits on the walls of the hot zone liner. Furthermore, it allows engaging the plasma plume downstream at temperature suitable for optimal processing of powders through precise targeting of temperature level and residence time. For example, there is the ability to dial the length of the plume using microwave powder, gas flows, and pressure in the quenching vessel that contains the plasma plume.

Generally, the downstream spheroidization method can utilize two main hardware configurations to establish a stable plasma plume which are: annular torch, such as described in U.S. Pat. Pub. No. 2018/0297122, or swirl torches described in U.S. Pat. No. 8,748,785 B2 and U.S. Pat. No. 9,932,673 B2, each of which is hereby incorporated by reference in its entirety. A feed system close-coupled with the plasma plume at the exit of the plasma torch is used to feed powder axisymmetrically to preserve process homogeneity.

Other feeding configurations may include one or several individual feeding nozzles surrounding the plasma plume. The feedstock powder can enter the plasma at a point from any direction and can be fed in from any direction, 360° around the plasma, into the point within the plasma. The feedstock powder can enter the plasma at a specific position along the length of the plasma plume where a specific temperature has been measured and a residence time estimated for sufficient melting of the particles. The melted particles exit the plasma into a sealed chamber where they are quenched then collected.

The feed materials 514 can be introduced into a microwave plasma torch 502. A hopper 506 can be used to store the feed material 514 before feeding the feed material 514 into the microwave plasma torch 502, plume, or exhaust via inlet 508. The feed material 514 can be injected at any angle to the longitudinal direction of the plasma torch 502, such as at 5, 10, 15, 20, 25, 30, 35, 40, 45, 50, 55 degrees, or any value between the aforementioned values. In some embodiments, the feedstock can be injected an angle of greater than 5, 10, 15, 20, 25, 30, 35, 40, 45, 50, or 55 degrees. In some embodiments, the feedstock can be injected an angle of less than 5, 10, 15, 20, 25, 30, 35, 40, 45, 50, or 55 degrees. In alternative embodiments, the feedstock can be injected along the longitudinal axis of the plasma torch.

The microwave radiation can be brought into the plasma torch through a waveguide 504. The feed material 514 may be fed into a plasma chamber 510 and may be placed into contact with the plasma generated by the plasma torch 502. When in contact with the plasma, plasma plume, or plasma exhaust, the feed material may melt. While still in the plasma chamber 510, the feed material 514 cools and solidifies before being collected into a container 512. Alternatively, the feed material 514 can exit the plasma chamber 510 while still in a melted phase and cool and solidify outside the plasma chamber. In some embodiments, a quenching chamber may be used, which may or may not use positive pressure. While described separately from FIG. 1, the embodiments of FIGS. 5A and 5B are understood to use similar features and conditions to the embodiment of FIG. 4.

Microwave Plasma Processing

In a microwave plasma process, the feedstock may be entrained in an inert and/or reducing gas environment and injected into the microwave plasma, the microwave plasma plume, or the microwave plasma exhaust. Upon injection into a hot plasma (or plasma plume or exhaust), the feedstock may undergo a physical and/or chemical transformation (e.g., spheroidization). After processing, the resulting material may be released into a chamber filled with an inert gas and directed into hermetically sealed drums where is it stored. This process can be carried out at atmospheric pressure, in a partial vacuum, or at a slightly higher pressure than atmospheric pressure.

In alternative embodiments, the process can be carried out in a low, medium, or high vacuum environment. The process can run in batches or continuously, with the drums being replaced as they fill up with processed material. By controlling the process parameters, such as cooling gas flow rate, residence time, plasma conditions, cooling gas composition, various material characteristics can be controlled.

Residence time of the particles within a hot zone of the plasma can also be adjusted to provide control over the resulting material characteristics. That is, the length of time the particles are exposed to the plasma determines the extent of melting of the feedstock particles (i.e., surface of the particle melted as compared to the inner most portion or core of the particle). Residence time can be adjusted by adjusting such operating variables of particle injection rate and flow rate (and conditions, such as laminar flow or turbulent flow) within the hot zone. Equipment changes can also be used to adjust residence time. For example, residence time can be adjusted by changing the cross-sectional area of the plasma, by, for example, extending the plasma. In some embodiments, extending the plasma may comprise incorporating an extension tube into the microwave plasma apparatus.

In some embodiments, the extension tube may comprise a stepped shape, such that the tube comprises one or more cylindrical volumes extending downward in the reaction chamber, wherein each successive cylindrical volume comprises a larger diameter than each previous cylindrical volume as the tube extends downward in the reaction chamber. In some embodiments, the extension tube may have a conical shape, tapering radially outwards as it extends downward into the reaction chamber. In some embodiments, the extension tube may comprise a single cylindrical volume 4. In some embodiments, the feed material inlets may insert feedstock within the extension tube.

In some embodiments, the extension tube may comprise a length of about 1 foot. In some embodiments, the extension tube may comprise a length of about 1 inch, about 2 inches, about 3 inches, about 4 inches, about 5 inches, about 6 inches, about 7 inches, about 8 inches, about 9 inches, about 10 inches, about 11 inches, about 1 foot, about 2 feet, about 3 feet, about 4 feet, about 5 feet, about 6 feet, about 7 feet, about 8 feet, about 9 feet, about 10 feet, about 11 feet, about 12 feet, about 13 feet, about 14 feet, about 15 feet, about 16 feet, about 17 feet, about 18 feet, about 19 feet, about 20 feet, about 21 feet, about 22 feet, about 23 feet, about 24 feet, about 25 feet, about 26 feet, about 27 feet, about 28 feet, about 29 feet, or about 30 feet, or any value between the aforementioned values.

In some embodiments, the feedstock particles are exposed to a temperature profile at between 4,000 and 8,000 K within the microwave plasma. In some embodiments, the particles are exposed to a temperature profile at between 3,000 and 8,000 K within the microwave plasma. In some embodiments, one or more temperature sensors may be located within the microwave plasma torch to determine a temperature profile of the plasma.

Examples

Tests were conducted using a microwave plasma apparatus comprising a 915 MHz microwave generator, a gas mixing panel, plasma torch with quartz liner, water-cooled stainless-steel reactor, water cooled exhaust and water separation particle filter. The monitoring instrumentation included a 1.3-megapixel machine vision camera, midbody type K thermocouple, inspection port at the liner exit, and mass spectrometer in the exhaust after the water-cooled sections. 3"ID/4" OD×6" long tube made of E+25 isomolded graphite was used as the extension and held up by 304 stainless sheet scaffold. The top edge was machined to fit over the quartz liner to create a seamless extension of the plasma containment.

All tests were operated at atmospheric pressure (760 Torr). Before running, the chamber was purged to below 100 ppm oxygen using argon gas before striking plasma. After the tests and once the chamber temperature had fallen below 50 C, compressed dry air (CDA) was slowly added in 5 vol % increments with Argon until 100 vol % CDA filled the chamber. Table 2 lists process conditions for the various tests.

TABLE 2

Test Process Conditions

| Test | Power, net kW | $H_2$ Vol % | Ar Vol % | $CH_4$ Vol % | Flow Rate SCFM (Ar) | Runtime (min) |
|---|---|---|---|---|---|---|
| 1a | 8 | 20 | 0 | 80 | 5 | <1 |
| 1b | 12.5 | 20 | 75-77 | 3-5 | 9 | 20 |
| 2 | 12.5 | 20 | 77 | 3 | 9 | 10 |

Tests 1a and 1b were conducted to determine the plasma stability of methane gas in a microwave plasma. An argon/hydrogen plasma was run at 10 kW of power. The plasma composition was to be shifted from 20 vol % to 100 vol % hydrogen. Once stable, 100% hydrogen plasma was established, and the methane composition was raised with the goal of 100% methane plasma.

Maximum flow conditions and minimum flow conditions were used to evaluate the effect on CNT synthesis as well as conversion efficiency of methane into C and $H_2$. The results of this test were used to determine the optimum operating conditions for Test 2. Additionally, soot samples were collected from the chamber cover, chamber walls, and collection cup and were evaluated for morphology of the carbon and any presence of CNTs.

Test 2 utilized the stable plasma conditions and integrated a graphite extension tube at the plasma liner exit. High and low methane decomposition conditions were to be tested and samples taken. Table 2 lists the process conditions used for the testing.

The gas composition was sampled using a MKS Cirrus 3 Mass Spectrometer operating at 40 kV and sampling from 1-50 AMU. The gas sample was taken at the end of the water-cooled exhaust to ensure all products were stable. Fragmentation patterns for hydrogen, methane, acetylene, and argon gas were taken from the NIST database and summed to determine composition of the exhaust. Soot samples were collected dry from the cover, wall, and collection cup of the chamber. The samples were inspected using a field emission scanning electron microscope (FE-SEM) to evaluate morphology. Carbon samples were suspended in isopropyl alcohol and sonicated for 5 minutes. The solution was deposited onto a single crystal silicon substrate and let dry at room temperature. To determine carbon form, the sample was evaluated using an x-ray diffractometer.

In Test 1a. Argon supply was switched directly to methane during the running (80 vol % $CH_4$, 20 vol % $H_2$). The power was set to 10 KW and the flows were 5 SCFM (measured as "methane"). The plasma was run for approximately 1 minute before extinguishing. Inspection revealed significant fowling of the quartz liner. Run length was insufficient to receive mass spectrometer data or carbon samples. The glowing liner indicated the liner temperature was exceeding 800° C. The soot was wiped away from the outside of the liner and the arcing pattern was facing the incident wave from the microwave generator.

Figure 6:
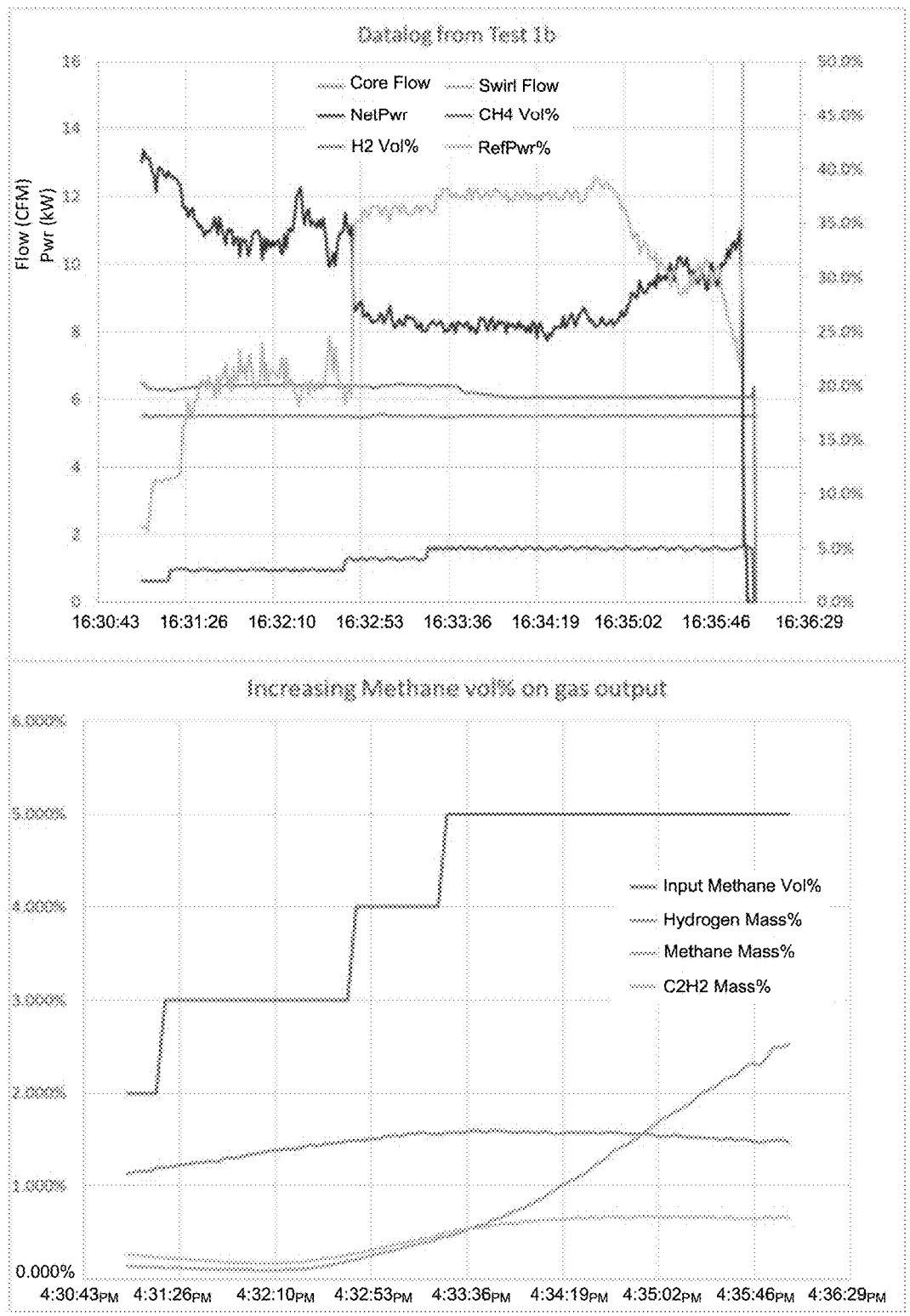
FIG. 6 illustrates mass spectrometer results for methane level testing according to some embodiments herein.

In Test 1b, methane was added to a stable Ar:$H_2$ plasma at low levels and increased until plasma stability suffered. 3 vol % methane in 20 vol % $H_2$:Ar at 13 kW was found to be the most stable condition. Increasing to 4 vol % methane resulted in high reflected power which required retuning of the microwave circuit and continuing further to 5 vol % methane resulted in abrupt failures of the plasma. FIG. 6 illustrates mass spectrometer results for the methane level testing.

As methane level was increased, total hydrogen production appears to have plateaued at a 3 vol % methane plasma and acetylene production at a 4 vol % methane plasma. The microwave circuit required tuning to bring coupled power back to 13 kW between 3 and 4 vol %. Even with tuning, plasma diameter may compress significantly with increased methane levels. Stable conditions determined during this test were then run until equilibrium in the gas products was seen from the mass spectrometer. This required approximately 10 minutes of run time.

Figure 7:
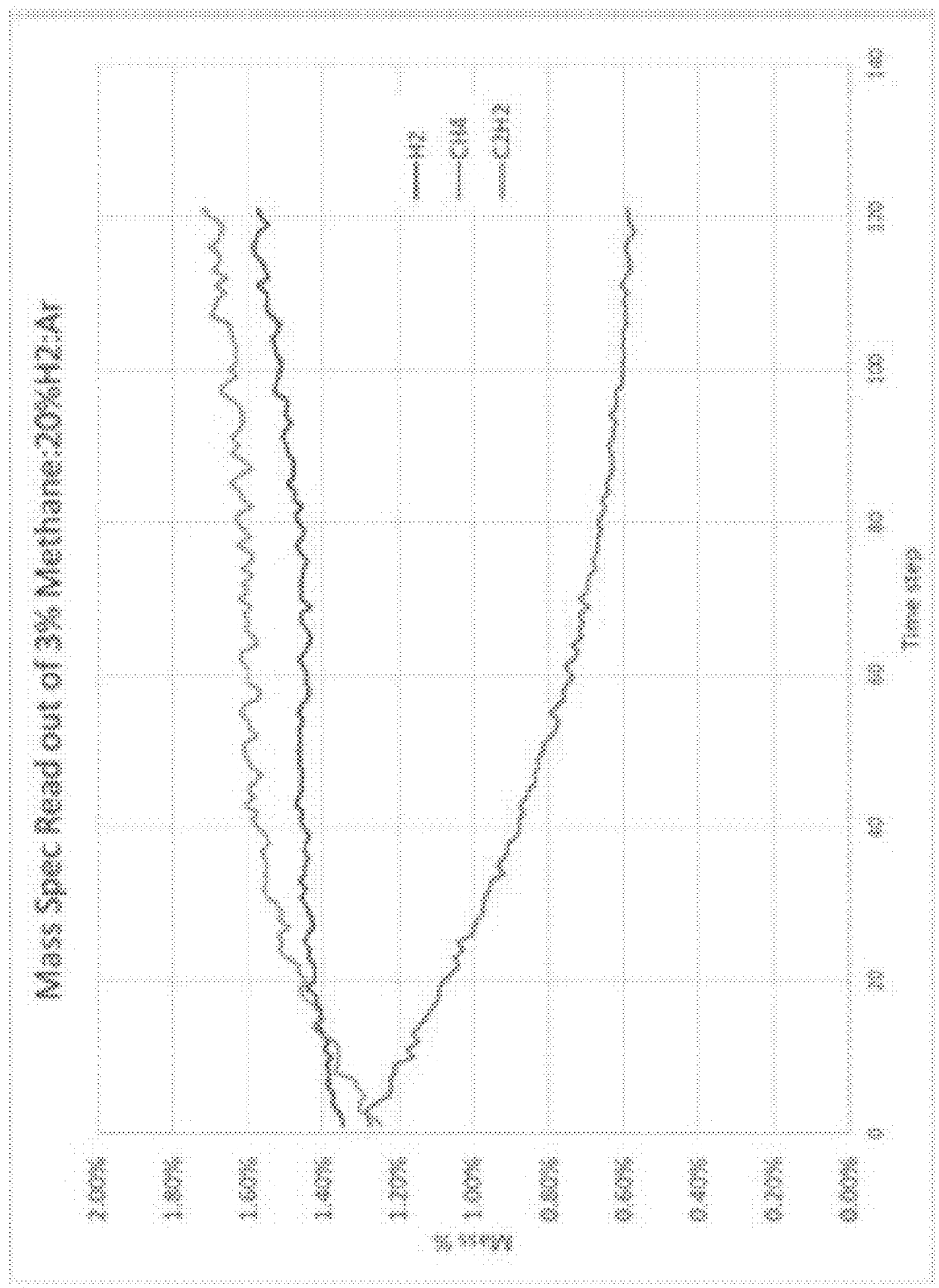
FIG. 7 illustrates equilibrium mass spectrum data taken during Test 1b according to some embodiments herein.

FIG. 7 illustrates equilibrium mass spectrum data taken during Test 1b. The total methane conversion was approximately 60%. Hydrogen levels increased from about 1.27 wt. % to about 1.58 wt. % and acetylene level ended at 1.72 wt. %.

Figure 8:
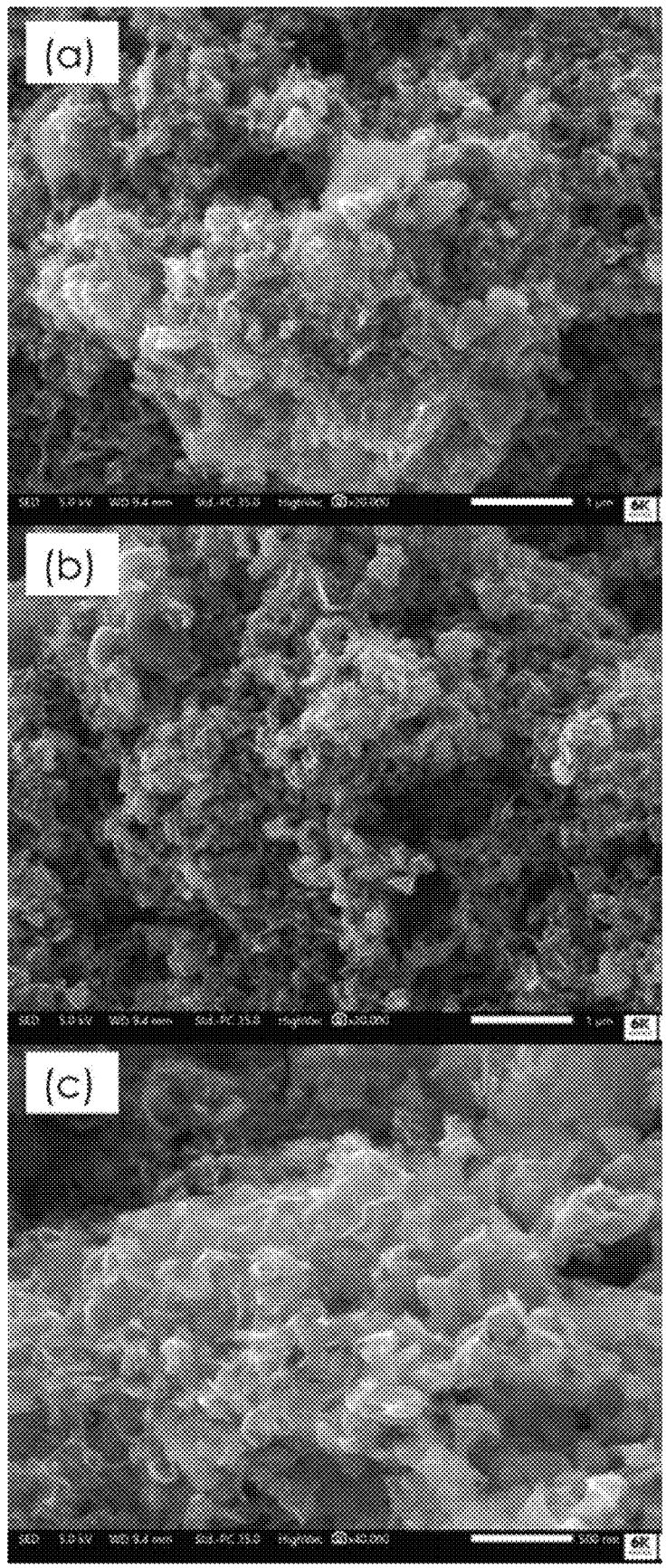
FIG. 8 illustrates FESEM images taken of the carbon sample of Test 1b according to some embodiments herein.

Carbon samples were taken from the cover and walls of the reactor. The total mass of sample material was less than 1 gram. Under FESEM magnification, the structure can be seen in FIG. 8 as primarily sheet or platelet like with little spherical amorphous carbon black in the field of view. No tube-like structures were observed. Exposed sheet edges measure several hundred nanometers on average. It should be noted that at higher excitation voltages above 10 kV, significant interference was observed due to material charging.

Figure 9:
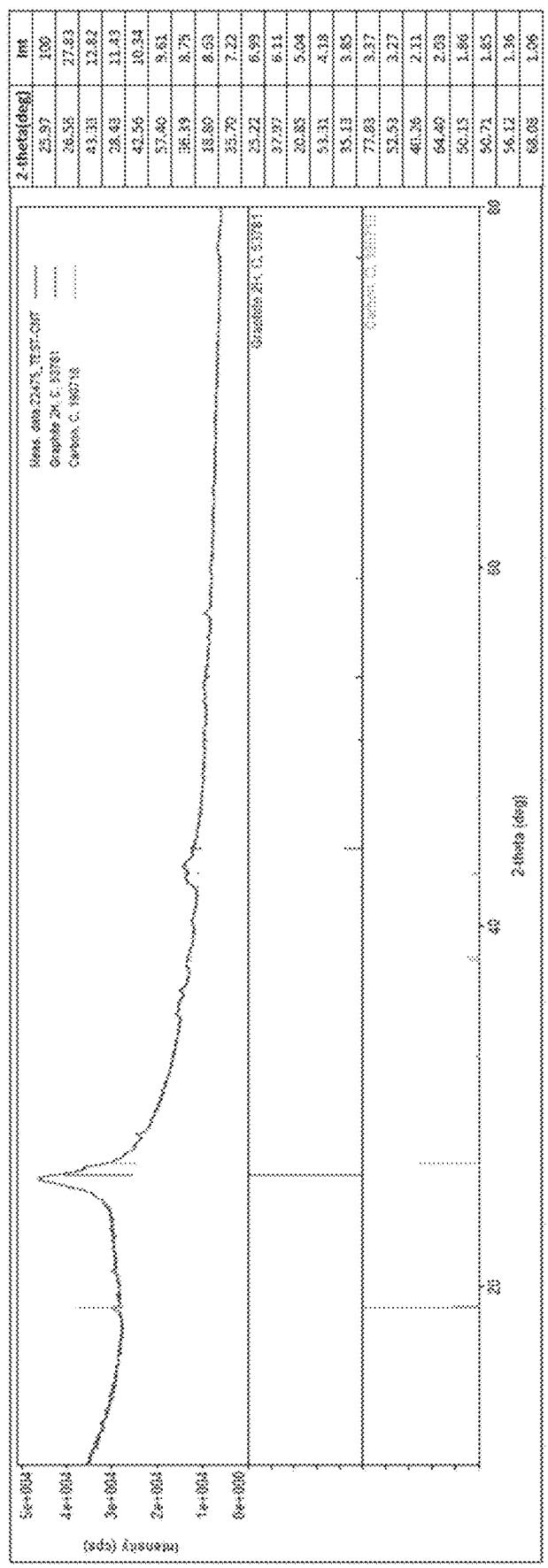
FIG. 9 illustrates an x-ray diffraction pattern from the carbon sample taken from Test 1b according to some embodiments herein.

X-ray diffraction results for the carbon sample are shown in FIG. 9. The characteristic peaks of graphite and carbon are also presented to compare to the recorded signal. Although the 25.97° peak is close to the primary graphite peak, it is slightly shifted. Additionally, the primary peak for carbon at 17° is absent from the recorded signal, indicating an absence of disordered carbon in the sample.

Figure 10:
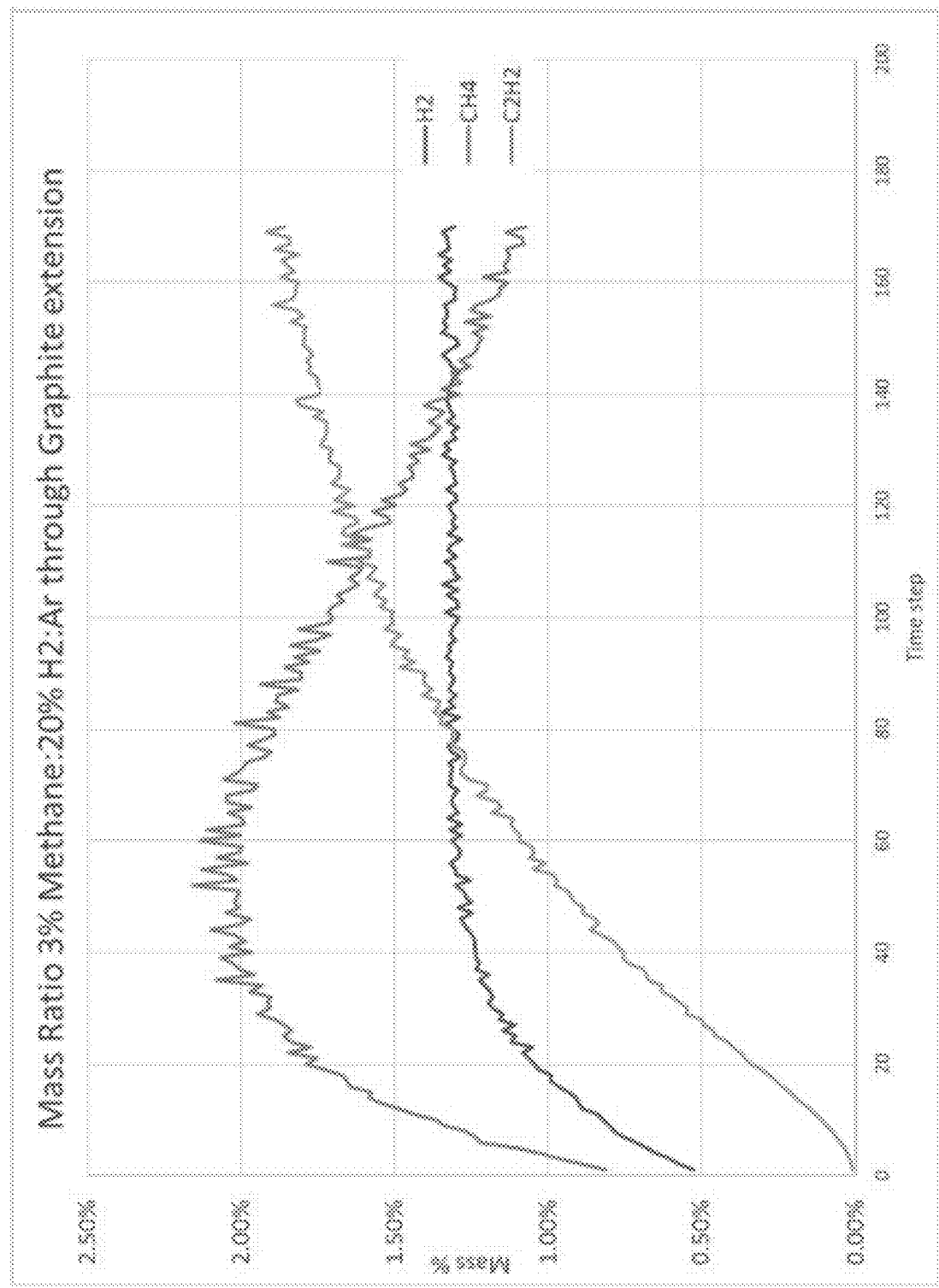
FIG. 10 illustrates mass spectrometry data from Test 2 through the graphite extension tube measured over 10 minutes according to some embodiments herein.

In Test 2. A graphite extension was installed and the stable plasma conditions from Test 1b were repeated. FIG. 10 illustrates mass spectrometry data from Test 2 through the graphite extension tube measured over 10 minutes. The hydrogen level increased only slightly from about 1.27 wt. % to about 1.35 wt. %. Acetylene peaked at 1.86 wt. % and methane continued to fall to 1.07 wt. % from a high of 2.16 wt. %. This signal was measured from the start of the plasma to the end of the test.

Figure 11:
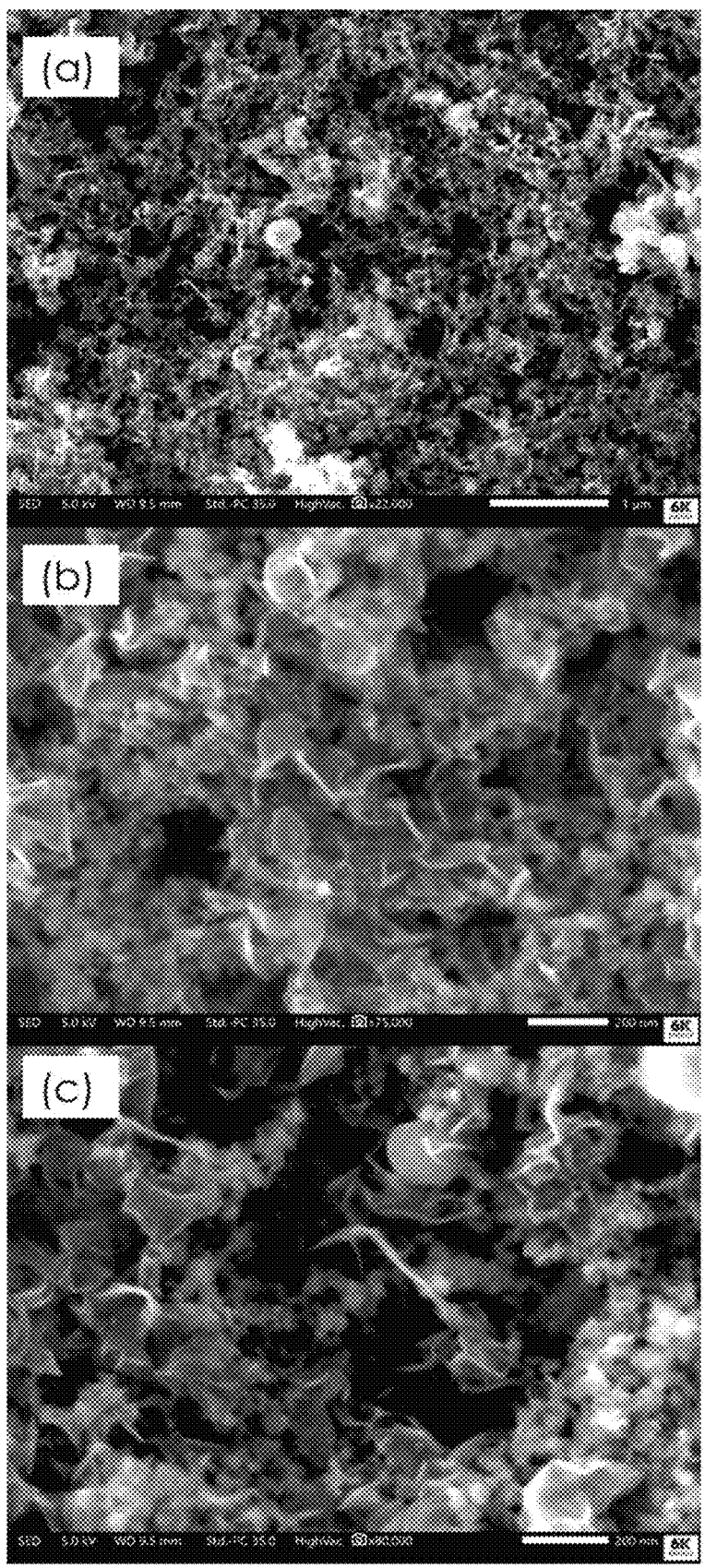
FIG. 11 illustrates FESEM images taken of the carbon sample of Test 2 according to some embodiments herein.

FESEM of the carbon samples collected from this test are shown in FIG. 11. Amorphous carbon/carbon black is seen in these samples as well as the sheet-like structure from test 1b. The average edge length was shorter than that seen in Test 1b and is closer to about 100 nm. No tube structures were observed.

In Test 1b, the rising hydrogen signal was a sign that some portion of the methane was converted to hydrogen and the strong acetylene signal was evidence that that the total energy or residence time of the methane was not high enough to completely pyrolyze to $H_2$ and carbon. Increasing the methane ratio in the plasma gases resulted in significant compression and increased reflected microwave energy. It was also noted that the plasma appeared hollow at low methane levels. It is possible that the carbon particles newly liberated from the methane gas acted to absorb or reflect the microwave energy like a conductor inserted into the microwave channel. This would explain the change in color of the plasma from a white/blue to a dull orange as the gas was no longer ionizing and instead the carbon was being heated and glowing.

While no nanotube formations were found from the testing, neither were the samples primarily amorphous carbon. Instead, the FESEM images appeared to show thin sheets which were crumpled over each other.

A critical outcome from these tests was the presence of a high concentration of nanoplatelet graphene from the pyrolysis of methane in a microwave plasma. The importance of hydrogen on the formation of gas phase nanographene most likely contributed to the creation of graphene over carbon nanotubes or carbon black.

Additional Embodiments

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

It will also be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein but are to be accorded the widest scope consistent with this disclosure, the principles and the novel features disclosed herein.

What is claimed is:

1. A method for producing a structured carbon powder using a microwave generated plasma, the method comprising:
    injecting a plasma gas comprising methane ($CH_4$) into a liner, the liner in communication with a microwave waveguide;
    propagating microwaves through the microwave waveguide, the microwaves generated using a microwave generator, wherein the microwave waveguide is oriented perpendicular to the liner;
    generating a microwave plasma by contacting the plasma gas with the microwaves;
    directing the microwave plasma through a graphite extension tube, the extension tube extending into a reaction chamber and confining the microwave plasma, and wherein the extension tube tapers radially outwards as it extends into the reaction chamber;
    wherein contacting the plasma gas with the microwaves pyrolyzes the plasma gas into pyrolysis products,
    wherein the pyrolysis products comprise hydrogen gas and solid carbon, and
    wherein the solid carbon comprises a sheet or platelet microstructure.

2. The method of claim 1, wherein a pressure within the liner is 760 Torr.

3. The method of claim 1, wherein a frequency of the microwaves is between about 300 MHz and about 300 GHz.

4. The method of claim 1, wherein a frequency of the microwaves is about 915 MHz.

5. The method of claim 1, wherein the liner comprises quartz.

6. The method of claim 1, wherein the methane comprises less than about 5 vol % of the plasma gas.

7. The method of claim 1, wherein the solid carbon comprises a sheet microstructure, and wherein edges of the carbon sheets measure between about 100 nm and about 1000 nm in length.

8. The method of claim 1, wherein the solid carbon comprises a sheet microstructure, and wherein edges of the carbon sheets measure between about 50 nm and about 150 nm in length.

9. The method of claim 1, wherein the solid carbon comprises no amorphous carbon.

10. The method of claim 1, wherein the solid carbon comprises no carbon nanotubes.

11. The method of claim 1, wherein the solid carbon comprises nanosheets of graphene.

12. The method of claim 1, wherein the pyrolysis products comprise acetylene ($C_2H_2$).

13. The method of claim 1, wherein the pyrolysis products comprise at least one of $CH_3$, $C_2H_5$, and $C_2H_3$.

14. The method of claim 1, wherein the plasma gas is contacted with the microwaves in the absence of a catalyst.

15. The method of claim 1, wherein the plasma gas comprises argon (Ar).

16. The method of claim 1, wherein the plasma gas comprises hydrogen ($H_2$).

17. The method of claim 1, wherein the plasma gas is injected into the liner at a temperature above 500° C.

18. The method of claim 1, wherein the solid carbon is solidified from a gas phase.

* * * * *